(12) United States Patent
Itescu et al.

(10) Patent No.: US 10,849,932 B2
(45) Date of Patent: *Dec. 1, 2020

(54) METHOD OF TREATING GRAFT VERSUS HOST DISEASE

(71) Applicant: Mesoblast, Inc., New York, NY (US)

(72) Inventors: Silviu Itescu, Melbourne (AU); Michael David Schuster, New York, NY (US)

(73) Assignee: MESOBLAST, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/131,975

(22) Filed: Sep. 14, 2018

(65) Prior Publication Data

US 2019/0030080 A1 Jan. 31, 2019

Related U.S. Application Data

(63) Continuation of application No. 15/055,221, filed on Feb. 26, 2016, now Pat. No. 10,105,394, which is a continuation of application No. 13/808,093, filed as application No. PCT/AU2011/000840 on Jul. 4, 2011, now Pat. No. 9,301,978.

(60) Provisional application No. 61/398,950, filed on Jul. 2, 2010.

(51) Int. Cl.
| | |
|---|---|
| *A61K 35/28* | (2015.01) |
| *A61P 37/02* | (2006.01) |
| *A61K 35/12* | (2015.01) |
| *C12N 5/0775* | (2010.01) |

(52) U.S. Cl.
CPC .............. *A61K 35/28* (2013.01); *A61P 37/02* (2018.01); *C12N 5/0663* (2013.01); *A61K 2035/122* (2013.01)

(58) Field of Classification Search
None
See application file for complete search history.

(56) References Cited

U.S. PATENT DOCUMENTS

| | | |
|---|---|---|
| 6,989,030 B1 | 1/2006 | Ohgushi |
| 2002/0116063 A1 | 8/2002 | Giannetti et al. |
| 2005/0123895 A1 | 6/2005 | Freund |
| 2011/0217263 A1 | 9/2011 | Itescu et al. |
| 2013/0171113 A1 | 7/2013 | Itescu et al. |
| 2013/0288362 A1 | 10/2013 | Noelle |
| 2015/0202232 A1 | 7/2015 | Itescu et al. |
| 2016/0361363 A1 | 12/2016 | Itescu et al. |

FOREIGN PATENT DOCUMENTS

| | | |
|---|---|---|
| WO | WO 2010/032092 A1 | 3/2006 |
| WO | WO 2008/036374 A2 | 3/2008 |
| WO | WO 2010/025506 A1 | 3/2010 |
| WO | WO 2010/057260 A1 | 5/2010 |

OTHER PUBLICATIONS

Siemionow et al, Semin Plast Surg, 2007, vol. 21, pp. 205-212.
Le Blanc et al. (2004), "Treatment of severe acute graft-versus-host disease with third party haploidentical mesenchymal stem cells", The Lancet 363:1439-1441.
Nasef et al. (2009) "Selected Stro-1-enriched bone marrow stromal cells display a major suppressive effect on lymphocyte proliferation", International Journal of Laboratory Hematology, 31:9-19.
Gronthos et al. (2003), "Molecular and cellular characterization of highly purified stromal stem cells derived from human bone marrow", Journal of Cell Science 116:1827-1835.
Gronthos et al. (2008), "A method to isolate and purify human bone marrow stromal stem cells", Methods in Molecular Biology 449:45-57.
International Search Report, dated Sep. 21, 2011 in connection with PCT International Application No. PCT/AU2011/000840, filed Jul. 4, 2011.
Supplementary European Search Report dated Nov. 12, 2013 in connection with European Application No. 11799995.3.
Francois et al. (2005), "Stro-1 positive and Stro-1 negative human mesenchymal stem cells express different levels of immunosuppression" Blood (ASH Annual Meeting Abstracts), 106:Abstract 2305.
Fang et al. (2007), "Human adipose tissue-derived mesenchymal stromal cells as salvage therapy for treatment of severe refractory acute graft-vs.-host disease in two children", Pediatric Transplantation 11:814-817.
Maitra et al. (2004), "Human mesenchymal stem cells support unrelated donor hematopoietic stem cells and suppress T-cell activation", Bone Marrow Transplantation 33:597-604.
Jan. 24, 2014 First Office Action issued in connection with Chinese Patent Application No. 201180042201.2 (English translation).
Zhang et al. (2007) "Immunosuppressive action of Stro-1+ and Stro-1-subgroups of human mesenchymal stem cells", Med. J. Chinese People's Liberation Army 32(1):1040-43.
International Search Report, dated Oct. 20, 2011 in connection with PCT International Application No. PCT/AU2011/000841, filed Jul. 4, 2011.
Supplementary European Search Report dated Nov. 7, 2013 in connection with European Application No. 11799996.1.
Jan. 29, 2014 First Office Action issued in connection with Chinese Patent Application No. 201180042207.X (English translation).
Office Action dated Jul. 20, 2015 in connection with Israeli Patent Application No. 224023.
Written Opinion of the Singaporean Patent Office dated Nov. 27, 2015 in connection with Singaporean Patent Application No. 201209047-8.

(Continued)

*Primary Examiner* — Allison M Fox
(74) *Attorney, Agent, or Firm* — John P. White; Gary J. Gershik

(57) ABSTRACT

A method for preventing the development of or treating GvHD complications in a mammalian patient which comprises administering to the mammal a population of cells enriched for STRO-1$^{bright}$ cells and/or progeny thereof and/or soluble factors derived therefrom.

13 Claims, 11 Drawing Sheets

Specification includes a Sequence Listing.

(56) References Cited

OTHER PUBLICATIONS

Bensidhoum et al. (2004), "Homing of in vitro expanded Stro-1⁻ or Stro-1⁺ human mesenchymal stem cells into the NOD/SCID mouse and their role in supporting human CD34 cell engraftment", Blood 103(9):3313-3319.

Nasef et al. (2007), "Identification of IL-10 and TGF-beta transcripts involved in the inhibition of T-lymphocyte proliferation during cell contact with human mesenchymal stem cells" Gene Expr. 13(4-5):217-226.

Office Action dated May 9, 2016 in connection with Japanese Application No. 2013-516910 (English translation).

Psaltis et al. (2010), "Enrichment for STRO-1 Expression Enhances the Cardiovascular Paracrine Activity of Human Bone Marrow-Derived Mesenchymal Cell Populations", J. Cell Physiol. 223(2):530-540.

Office Action dated Sep. 22, 2014 in connection with U.S. Appl. No. 13/808,093.

Mar. 23, 2015 Amendment in Response to Office Action dated Sep. 22, 2014 in connection with U.S. Appl. No. 13/808,093.

Mar. 30, 2015 Supplemental Amendment in Response to Office Action dated Sep. 22, 2014 in connection with U.S. Appl. No. 13/808,093.

Office Action dated Jun. 22, 2015 in connection with U.S. Appl. No. 13/808,093.

Sep. 15, 2015 Amendment in Response to Office Action dated Jun. 22, 2015 in connection with U.S. Appl. No. 13/808,093.

Notice of Allowance dated Nov. 23, 2015 in connection with U.S. Appl. No. 13/808,093.

Office Action dated May 27, 2015 in connection with U.S. Appl. No. 13/808,092.

Oct. 19, 2015 Amendment in Response to Office Action dated May 27, 2015 in connection with U.S. Appl. No. 13/808,092.

Office Action dated Nov. 10, 2015 in connection with U.S. Appl. No. 13/808,092.

Feb. 10, 2016 Amendment in Response to Office Action dated Nov. 10, 2015 in connection with U.S. Appl. No. 13/808,092.

Advisory Action dated Feb. 17, 2016 in connection with U.S. Appl. No. 13/808,092.

May 10, 2016 Amendment in Response to Office Action dated Nov. 10, 2015 in connection with U.S. Appl. No. 13/808,092.

Office Action dated Nov. 17, 2016 in connection with U.S. Appl. No. 13/808,092.

METHOD OF TREATING GRAFT VERSUS HOST DISEASE

CROSS-REFERENCE TO RELATED APPLICATIONS

This application is a continuation of U.S. application Ser. No. 15/055,221, filed Feb. 26, 2016, which is a continuation of U.S. application Ser. No. 13/808,093, filed Mar. 14, 2013, now U.S. Pat. No. 9,301,978, issued May 4, 2016, which is a § 371 national stage of PCT International Application No. PCT/AU2011/000840, filed Jul. 4, 2011, claiming the benefit of U.S. Provisional Application No. 61/398,950, filed Jul. 2, 2010, the contents of each of which are hereby incorporated by reference into the application.

REFERENCE TO SEQUENCE LISTING

This application incorporates-by-reference nucleotide and/or amino acid sequences which are present in the file named "180914_81809-AAA-PCT-US_Sequence_Listing_CAE.txt", which is 7.27 kilobytes in size, and which was created Sep. 14, 2018 in the IBM-PC machine format, having an operating system compatibility with MS-Windows, which is contained in the text file filed Sep. 14, 2018 as part of this application.

FIELD

This invention relates to methods for enhancing the engraftment of hematopoietic progenitor cells, enhancing bone marrow transplantation and preventing or reducing graft versus host disease. In one embodiment the invention relates to preventing or alleviating the complications following allogeneic bone marrow transplantation, namely graft versus host disease in mammalian patients, especially in human patients.

BACKGROUND

Bone marrow transplantation is indicated following a process which destroys bone marrow. For example, following intensive systemic radiation or chemotherapy, bone marrow is the first target to fail. Metastatic cancers are commonly treated with very intensive chemotherapy, which is intended to destroy the cancer, but also effectively destroys the bone marrow. This induces a need for bone marrow transplantation. Alleviation of any but the most acute life-threatening conditions involving bone marrow disorders with bone marrow transplantation is, however, generally regarded as too risky, because of the likelihood of the onset of graft versus host disease (GvHD).

GvHD is an immunological disorder that is the major factor that limits the success and availability of allogeneic bone marrow or stem cell transplantation. GvHD is a systemic inflammatory reaction which causes chronic illness and may lead to death of the host mammal. At present, allogeneic transplants invariably run a severe risk of associated GvHD, even where the donor has a high degree of histocompatibility with the host.

GvHD is caused by donor T-cells reacting against systemically distributed incompatible host antigens, causing powerful inflammation. In GvHD, mature donor T-cells that recognize differences between donor and host become systemically activated. Current methods to prevent and treat GvHD involve administration of drugs such as cyclosporin-A and corticosteroids. These have serious side effects, must be given for prolonged periods of time, and are expensive to administer and to monitor. Attempts have also been made to use T-cell depletion to prevent GvHD, but this requires sophisticated and expensive facilities and expertise. Too great a degree of T-cell depletion leads to serious problems of failure of engraftment of bone marrow stem cells, failure of hematopoietic reconstitution, infections, or relapse. More limited T-cell depletion leaves behind cells that are still competent to initiate GvHD. As a result, current methods of treating GvHD are only successful in limited donor and host combinations, so that many patients cannot be offered potentially life-saving treatment.

Mesenchymal stem cells (MSC) exhibit a potent immunosuppressive activity which has been successfully exploited in the clinical setting to treat graft-versus-host disease (GvHD), an otherwise lethal complication of bone marrow transplantation. Because of the limited characterization, MSC preparations are quite heterogenous and this limits the magnitude of their immunosuppression and therefore the clinical benefit.

SUMMARY

In work leading up to the present invention, the inventors compared mesenchymal stem cell and STRO-1$^{bright}$ multipotential cell preparations in terms of their effect on GvHD. Surprisingly, the Stro-1$^{bright}$ multipotential cell preparation was vastly superior to the mesenchymal stem cell preparation in ameliorating GvHD.

Accordingly the present invention provides a method for alleviating the development of GvHD complications in a mammalian patient which comprises administering to the patient a population of cells enriched for STRO-1$^{bright}$ cells and/or progeny thereof and/or soluble factors derived therefrom.

In one embodiment the mammalian patient is undergoing or about to undergo a bone marrow transplant.

In another embodiment the present invention provides a method for of alleviating the development of GvHD complications in a mammalian patient caused by bone marrow transplantation which comprises administering to the patient (a) precursors of bone marrow lineage cells, and (b) a population of cells enriched for STRO-1$^{bright}$ cells and/or progeny thereof and/or soluble factors derived therefrom, wherein the population of cells enriched for STRO-1$^{bright}$ cells and/or progeny thereof and/or soluble factors derived therefrom is/are administered in an amount effective to reduce the severity of GvHD in the patient.

In one embodiment, the graft-versus-host disease is a result of a T cell immune response. In one example, the T cells are from a donor and the antigen is from the recipient. For example, the T cells may be present in a transplant. In another embodiment, the T cells are from the recipient and the antigen is from the donor.

In another embodiment of this method the STRO-1$^{bright}$ cells and/or progeny cells thereof and/or soluble factors derived therefrom are genetically engineered to express a molecule to block co-stimulation of T-cells.

The STRO-1$^{bright}$ cells may be autogeneic or allogeneic. In one embodiment, the STRO-1$^{bright}$ cells are allogeneic.

In another embodiment of this method, the STRO-1$^{bright}$ cells and/or progeny cells thereof have been expanded in culture prior to administration or to obtaining the soluble factors.

Exemplary dosages of the cells include between 0.1×10$^6$ to 5×10$^6$ STRO-1$^{bright}$ cells and/or progeny thereof. For example, the method comprises administering between 0.3× $10^6$ to 2×$10^6$ STRO-1$^{bright}$ cells and/or progeny thereof.

One form of the method involves administering a low dose of STRO-1$^{bright}$ cells and/or progeny thereof. Such a low dose is, for example, between 0.1×$10^5$ and 0.5×$10^6$ STRO-1$^{bright}$ cells and/or progeny thereof, such as about 0.3×$10^6$ STRO-1$^{bright}$ cells and/or progeny thereof.

The present disclosure also contemplates numerous administrations of the cells and/or soluble factors. For example, such a method can involve administering the cells and monitoring the subject to determine when one or more symptoms of GvHD occurs or recurs and administering a further dose of the cells and/or soluble factors. Suitable methods for assessing symptoms of GvHD will be apparent to the skilled artisan and/or described herein.

In one example, the population enriched for STRO-1$^{bright}$ cells and/or progeny thereof and/or soluble factors derived therefrom are administered once weekly or less often, such as, once every four weeks or less often.

In another embodiment, the population of cells enriched for STRO-1$^{bright}$ cells and/or progeny cells thereof and/or soluble factors derived therefrom is administered systemically. For example, the population of cells enriched for Stro-1$^{bri}$ cells and/or progeny cells thereof and/or soluble factors derived therefrom may be administered intravenously, intra-arterially, intramuscularly, subcutaneously, into an aorta, into an atrium or ventricle of the heart or into a blood vessel connected to an organ, e.g., an abdominal aorta, a superior mesenteric artery, a pancreaticoduodenal artery or a splenic artery.

In another embodiment the methods of the invention further comprise administering an immunosuppressive agent. The immunosuppressive agent may be administered for a time sufficient to permit said transplanted cells to be functional. In one example, the immunosuppressive agent is cyclosporine. The cyclosporine may be administered at a dosage of from 5 to 40 mg/kg body wt.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

DETAILED DESCRIPTION

Figure 1:
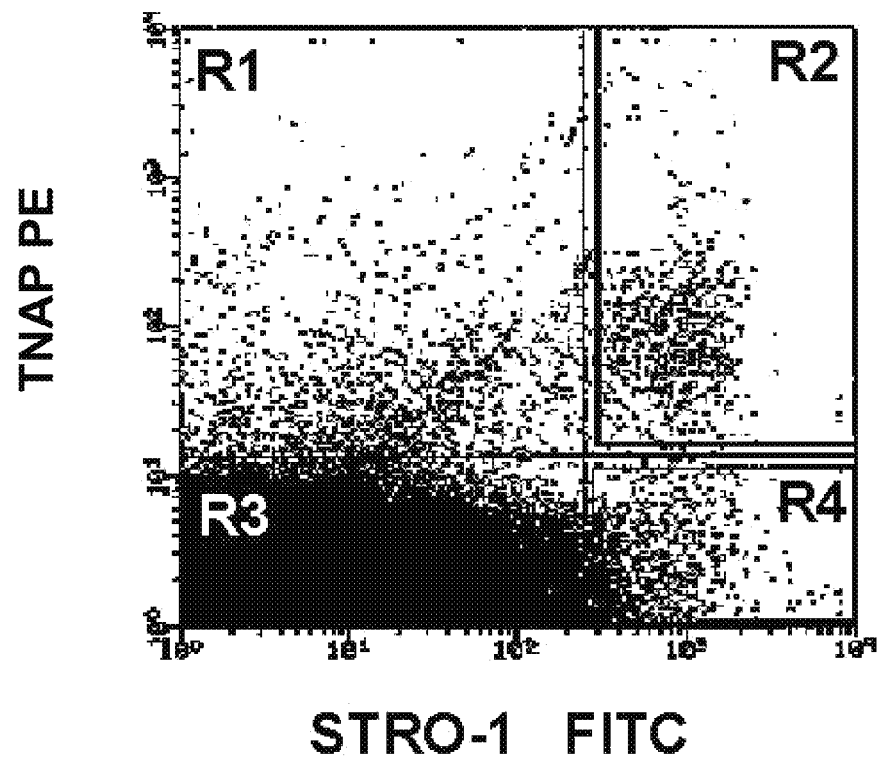
FIG. 1. Co-expression of TNAP (STRO-3) and the Mesenchymal Precursor Cell Marker, STRO-1$^{bright}$ by Adult Human BMMNC. Dual-color immunofluorescence and flow cytometry was performed by incubation of STRO-1 MACS-selected BMMNC and indirectly labelled with a goat anti-murine IgM antibody coupled to FITC (x axis), and STRO-3 mAb (murine IgG1) indirectly labelled with a goat anti-murine IgG coupled to PE (y axis). The dot plot histogram represents 5×$10^4$ events collected as listmode data. The vertical and horizontal lines were set to the reactivity levels of <1.0% mean fluorescence obtained with the isotype-matched control antibodies, 1B5 (IgG) and 1A6.12 (IgM) treated under the same conditions. The results demonstrate that a minor population of STRO-1$^{bright}$ cells co-expressed TNAP (upper right quadrant) while the remaining STRO-1+ cells failed to react with the STRO-3 mAb.

Results presented herein show that a population of cells enriched for STRO-1$^{bright}$ cells was unexpectedly vastly superior to a STRO-1 negative mesenchymal stem cell preparation in ameliorating GvHD.

Accordingly the present invention provides a method for alleviating the development of GvHD complications in a mammalian patient which comprises administering comprising administering to the patient a population of cells enriched for STRO-1$^{bright}$ cells and/or progeny thereof and/or soluble factors derived therefrom.

For example, the invention provides a method for of alleviating the development of GvHD complications in a mammalian patient caused by bone marrow transplantation which comprises administering to the patient (a) precursors of bone marrow lineage cells, and (b) a population of cells enriched for STRO-1$^{bright}$ cells and/or progeny thereof and/or soluble factors derived therefrom, wherein the population of cells enriched for Stro-1$^{bright}$ cells and/or progeny thereof and/or soluble factors derived therefrom is/are administered in an amount effective to reduce the severity of GvHD in the patient.

As used herein, the term "soluble factors" shall be taken to mean any molecule, e.g., protein, peptide, glycoprotein, glycopeptide, lipoprotein, lipopeptide, carbohydrate, etc. produced by STRO-1$^{bright}$ cells and/or progeny thereof that are water soluble. Such soluble factors may be intracellular and/or secreted by a cell. Such soluble factors may be a complex mixture (e.g., supernatant) and/or a fraction thereof and/or may be a purified factor. In one embodiment of the present invention soluble factors are or are contained within supernatant. Accordingly, any embodiment herein directed to administration of one or more soluble factors shall be taken to apply mutatis mutandis to the administration of supernatant.

The methods of the invention may involve administration of population of cells enriched for STRO-1$^{bright}$ cells and/or progeny cells thereof alone, and/or soluble factors derived therefrom. The methods of the invention may also involve administration of progeny cells alone, or soluble factors derived from the progeny cells. The methods of the invention may also involve administration of a mixed population of STRO-1$^{bright}$ cells and progeny cells thereof, or soluble factors from a mixed culture of STRO-1$^{bright}$ cells and progeny cells thereof.

A preferred application of this invention is to humans, however, it is expected that the invention is also applicable to animals, and these might include agricultural animals such as cows, sheep, pigs and the like, domestic animals such as dogs, cats, laboratory animals such as mice, rats, hamsters and rabbits or animals that might be used for sport such as horses.

Thus, STRO-1$^{bright}$ cells and/or progeny cells thereof and/or soluble factors derived therefrom can be used to condition a recipient's immune system to donor or foreign bone marrow cells by administering to the recipient, prior to, or at the same time as transplantation of the donor cells, STRO-1$^{bright}$ cells and/or progeny cells thereof and/or soluble factors derived therefrom in an amount effective to reduce or eliminate an immune response against the transplant by the recipient's T cells. The STRO-1$^{bright}$ cells and/or progeny cells thereof and/or soluble factors derived therefrom affect the T cells of the recipient such that the T cell response is reduced or eliminated when presented with donor or foreign tissue.

Thus, in the context of bone marrow (hematopoietic stem cell) transplantation, attack of the host by the graft can be reduced or eliminated. Donor marrow can be pretreated with recipient STRO-1$^{bright}$ cells and/or progeny cells thereof and/or soluble factors derived therefrom prior to implant of the bone marrow or peripheral blood stem cells into the recipient. In a preferred embodiment, the donor marrow is first exposed to recipient tissue/cells and then treated with STRO-1$^{bright}$ cells and/or progeny cells thereof and/or soluble factors derived therefrom. Although not being limited thereto, it is believed that the initial contact with recipient tissue or cells functions to activate the T cells in the marrow. Subsequent treatment with the STRO-1$^{bright}$ cells and/or progeny cells thereof and/or soluble factors derived therefrom inhibits or eliminates further activation of the T cells in the marrow, thereby reducing or eliminating an adverse affect by the donor tissue, i.e. the therapy reduces or eliminates graft versus host response.

In a further embodiment, a transplant recipient suffering from graft versus host disease may be treated to reduce or eliminate the severity thereof by administering to such recipient STRO-1$^{bright}$ cells and/or progeny cells thereof and/or soluble factors derived therefrom autologous or allogeneic to the donor, which allogeneic cells can be STRO-1$^{bright}$ cells and/or progeny cells thereof autologous to the recipient or third party STRO-1$^{bright}$ cells and/or progeny cells thereof, in an amount effective to reduce or eliminate a graft rejection of the host. The STRO-1$^{bright}$ cells and/or progeny cells thereof and/or soluble factors derived therefrom inhibit or suppress the activated T cells in the donor tissue from mounting an immune response against the recipient, thereby reducing or eliminating a graft versus host response.

The recipient's STRO-1$^{bright}$ cells and/or progeny cells thereof and/or soluble factors derived therefrom may be obtained from the recipient prior to the transplantation and may be stored and/or culture-expanded to provide a reserve of STRO-1$^{bright}$ cells and/or progeny cells thereof and/or soluble factors derived therefrom in sufficient amounts for treating an ongoing graft attack against host.

It is further contemplated that only a single treatment with the STRO-1$^{bright}$ cells and/or progeny cells thereof and/or soluble factors derived therefrom of the present invention may be required, eliminating the need for chronic immunosuppressive drug therapy. Alternatively, multiple administrations of Stro-1$^{bri}$ cells and/or progeny cells thereof and/or soluble factors derived therefrom may be employed.

The dosage of the STRO-1$^{bright}$ cells and/or progeny cells thereof and/or soluble factors derived therefrom varies within wide limits and will, of course be fitted to the individual requirements in each particular case. In general, in the case of parenteral administration, it is customary to administer from about 0.01 to about 5 million cells per kilogram of recipient body weight. The number of cells used will depend on the weight and condition of the recipient, the number of or frequency of administrations, and other variables known to those of skill in the art The cells can be suspended in an appropriate diluent, at a concentration of from about 0.01 to about $5 \times 10^6$ cells/ml. One form of the method involves administering a low dose of STRO-1$^{bright}$ cells and/or progeny thereof. Such a low dose is, for example, between $0.1 \times 10^5$ and $0.5 \times 10^6$ STRO-1$^{bright}$ cells and/or progeny thereof, such as about $0.3 \times 10^6$ STRO-1$^{bright}$ cells and/or progeny thereof.

Suitable excipients for injection solutions are those that are biologically and physiologically compatible with the cells and with the recipient, such as buffered saline solution or other suitable excipients. The composition for administration is preferably formulated, produced and stored according to standard methods complying with proper sterility and stability.

The following examples further illustrate aspects of the present invention. However, they are in no way a limitation of the teachings or disclosure of the present invention as set forth herein.

STRO-1$^{bright}$ Cells or Progeny Cells, and Supernatant or One or More Soluble Factors Derived Therefrom STRO-1$^{bright}$ cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are typically capable of differentiating into germ lines such as mesoderm and/or endoderm and/or ectoderm. Thus, STRO-1$^{bright}$ cells are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. STRO-1$^{bright}$ cells are thus preferably non-hematopoietic progenitor cells which divide to yield daughter cells that are either stem cells or are precursor cells which in time will irreversibly differentiate to yield a phenotypic cell.

In a preferred embodiment, the STRO-1$^{bright}$ cells are enriched from a sample obtained from a subject, e.g., a subject to be treated or a related subject or an unrelated subject (whether of the same species or different). The terms 'enriched', 'enrichment' or variations thereof are used herein to describe a population of cells in which the proportion of one particular cell type or the proportion of a number of particular cell types is increased when compared with the untreated population.

In one embodiment the STRO-1$^{bright}$ cells are preferentially enriched relative to STRO-1$^{dim}$ or STRO-1$^{intermediate}$ cells.

In a preferred embodiment, the cells used in the present invention express one or more markers individually or collectively selected from the group consisting of TNAP$^+$, VCAM-1$^+$, THY-1$^+$, STRO-2$^+$, CD45$^+$, CD146$^+$, 3G5$^+$ or any combination thereof.

By "individually" is meant that the invention encompasses the recited markers or groups of markers separately, and that, notwithstanding that individual markers or groups of markers may not be separately listed herein the accompanying claims may define such marker or groups of markers separately and divisibly from each other.

By "collectively" is meant that the invention encompasses any number or combination of the recited markers or groups of peptides, and that, notwithstanding that such numbers or combinations of markers or groups of markers may not be specifically listed herein the accompanying claims may define such combinations or sub-combinations separately and divisibly from any other combination of markers or groups of markers.

Preferably, the STRO-1$^{bright}$ cells are additionally one or more of TNAP$^+$, VCAM-1$^+$, THY-1$^+$ STRO-2$^+$ and/or CD146$^+$.

A cell that is referred to as being "positive" for a given marker it may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This terms means that the marker is expressed at a relatively very low level by that cell, and that it generates a very low signal when detectably labelled or is undetectable above background levels.

The term "bright", when used herein, refers to a marker on a cell surface that generates a relatively high signal when detectably labelled. Whilst not wishing to be limited by theory, it is proposed that "bright" cells express more of the target marker protein (for example the antigen recognised by STRO-1) than other cells in the sample. For instance, STRO-1$^{bright}$ cells produce a greater fluorescent signal, when labelled with a FITC-conjugated STRO-1 antibody as determined by fluorescence activated cell sorting (FACS) analysis, than non-bright cells (STRO-1$^{dull/dim}$). Preferably, "bright" cells constitute at least about 0.1% of the most brightly labelled bone marrow mononuclear cells contained in the starting sample. In other embodiments, "bright" cells constitute at least about 0.1%, at least about 0.5%, at least about 1%, at least about 1.5%, or at least about 2%, of the most brightly labelled bone marrow mononuclear cells contained in the starting sample. In a preferred embodiment, STRO-1$^{bright}$ cells have 2 log magnitude higher expression of STRO-1 surface expression relative to "background", namely cells that are STRO-1⁻. By comparison, STRO-1$^{dim}$ and/or STRO-1$^{intermediate}$ cells have less than 2 log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In a preferred embodiment, the TNAP is BAP. In a particularly preferred embodiment, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in a preferred embodiment, the STRO-1$^{bright}$ cells are capable of giving rise to clonogenic CFU-F.

It is preferred that a significant proportion of the multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another embodiment, the Stro-1$^{bright}$ cells are not capable of giving rise, upon culturing, to hematopoietic cells.

In one embodiment, the cells are taken from the subject to be treated, cultured in vitro using standard techniques and used to obtain supernatant or soluble factors or expanded cells for administration to the subject as an autologous or allogeneic composition. In an alternative embodiment, cells of one or more of the established human cell lines are used. In another useful embodiment of the invention, cells of a non-human animal (or if the patient is not a human, from another species) are used.

The present invention also contemplates use of supernatant or soluble factors obtained or derived from STRO-1$^{bright}$ cells and/or progeny cells thereof (the latter also being referred to as expanded cells) which are produced from in vitro culture. Expanded cells of the invention may a have a wide variety of phenotypes depending on the culture conditions (including the number and/or type of stimulatory factors in the culture medium), the number of passages and the like. In certain embodiments, the progeny cells are obtained after about 2, about 3, about 4, about 5, about 6, about 7, about 8, about 9, or about 10 passages from the parental population. However, the progeny cells may be obtained after any number of passages from the parental population.

The progeny cells may be obtained by culturing in any suitable medium. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. A powder mixture that when mixed with water or other liquid becomes suitable for cell culture may be termed a "powdered medium".

In an embodiment, progeny cells useful for the methods of the invention are obtained by isolating TNAP⁺ STRO-1⁺ multipotential cells from bone marrow using magnetic beads labelled with the STRO-3 antibody, and then culture expanding the isolated cells (see Gronthos et al. *Blood* 85: 929-940, 1995 for an example of suitable culturing conditions).

In one embodiment, such expanded cells (progeny) (preferably, at least after 5 passages) can be TNAP⁻, CC9⁺, HLA class I⁺, HLA class II⁻, CD14⁻, CD19⁻, CD3⁻, CD11a⁻c⁻, CD31⁻, CD86⁻, CD34⁻ and/or CD80⁻. However, it is possible that under different culturing conditions to those described herein that the expression of different markers may vary. Also, whilst cells of these phenotypes may predominate in the expended cell population it does not mean that there is a minor proportion of the cells do not have this phenotype(s) (for example, a small percentage of the expanded cells may be CC9⁻). In one preferred embodiment, expanded cells still have the capacity to differentiate into different cell types.

In one embodiment, an expended cell population used to obtain supernatant or soluble factors, or cells per se, comprises cells wherein at least 25%, more preferably at least 50%, of the cells are CC9+.

In another embodiment, an expanded cell population used to obtain supernatant or soluble factors, or cells per se, comprises cells wherein at least 40%, more preferably at least 45%, of the cells are STRO-1⁺.

In a further embodiment, the expanded cells may express one or more markers collectively or individually selected from the group consisting of LFA-3, THY-1, VCAM-1, ICAM-1, PECAM-1, P-selectin, L-selectin, 3G5, CD49a/CD49b/CD29, CD49c/CD29, CD49d/CD29, CD 90, CD29, CD18, CD61, integrin beta 6-19, thrombomodulin, CD10, CD13, SCF, PDGF-R, EGF-R, IGF1-R, NGF-R, FGF-R, Leptin-R (STRO-2=Leptin-R), RANKL, STRO-1$^{bright}$ and CD146 or any combination of these markers.

In one embodiment, progeny cells derived from STRO-1$^{bright}$ cells are positive for the marker Stro-1$^{dim}$. These cells are referred to as Tissue Specific Committed Cells (TSCCs) and are more committed to differentiation than STRO-1$^{bri}$ cells are therefore less able to respond inductive factors. Non-limiting examples of the lineages to which TSCCs may be committed include hepatocyte progenitors, which are pluripotent for bile duct epithelial cells and hepatocytes; neural restricted cells, which can generate glial cell precursors that progress to oligodendrocytes and astrocytes, and neuronal precursors that progress to neurons; precursors for cardiac muscle and cardiomyocytes, glucose-responsive insulin secreting pancreatic beta cell lines. Other committed precursor cells include but are not limited to chondrocytes, osteoblasts, odontoblast, dentin-producing and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, osteoclast and haemopoietic-supportive stroma, cardiac muscle, smooth muscle, skeletal muscle, pericyte, vascular, epithelial, glial, neuronal, astrocyte and oligodendrocyte cells. Precursors include those that specifically can lead to connective tissue particularly including adipose, areolar, osseous, cartilaginous, elastic and fibrous connective tissues.

In another embodiment, the progeny cells are Multipotential Expanded STRO-1$^+$ Multipotential cells Progeny (MEMPs) as defined and/or described in WO 2006/032092. Methods for preparing enriched populations of STRO-1$^+$ multipotential cells from which progeny may be derived are described in WO 01/04268 and WO 2004/085630. In an in vitro context STRO-1$^+$ multipotential cells will rarely be present as an absolutely pure preparation and will generally be present with other cells that are tissue specific committed cells (TSCCs). WO 01/04268 refers to harvesting such cells from bone marrow at purity levels of about 0.1% to 90%. The population comprising MPCs from which progeny are derived may be directly harvested from a tissue source, or alternatively it may be a population that has already been expanded ex vivo.

For example, the progeny may be obtained from a harvested, unexpanded, population of substantially purified STRO-1$^+$ multipotential cells, comprising at least about 0.1, 1, 5, 10, 20, 30, 40, 50, 60, 70, 80 or 95% of total cells of the population in which they are present. This level may be achieved, for example, by selecting for cells that are positive for at least one marker individually or collectively selected from the group consisting of TNAP, STRO-1$^{bright}$, 3G5$^+$, VCAM-1, THY-1, CD146 and STRO-2.

MEMPS can be distinguished from freshly harvested STRO-1$^{bright}$ cells in that they are positive for the marker STRO-1$^{bright}$ and negative for the marker Alkaline phosphatase (ALP). In contrast, freshly isolated Stro-1$^{bri}$ cells are positive for both STRO-1$^{bright}$ and ALP. In a preferred embodiment of the present invention, at least 15%, 20%, 30%, 40%, 50%, 60%, 70%, 80%, 90% or 95% of the administered cells have the phenotype STRO-1$^{bri}$, ALP$^-$. In a further preferred embodiment the MEMPS are positive for one or more of the markers Ki67, CD44 and/or CD49c/CD29, VLA-3, α3β1. In yet a further preferred embodiment the MEMPs do not exhibit TERT activity and/or are negative for the marker CD18.

The STRO-1$^{bright}$ cell starting population may be derived from any one or more tissue types including bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon and skeletal muscle.

It will be understood that in performing the present invention, separation of cells carrying any given cell surface marker can be effected by a number of different methods, however, preferred methods rely upon binding a binding agent (e.g., an antibody or antigen binding fragment thereof) to the marker concerned followed by a separation of those that exhibit binding, being either high level binding, or low level binding or no binding. The most convenient binding agents are antibodies or antibody-based molecules, preferably being monoclonal antibodies or based on monoclonal antibodies because of the specificity of these latter agents. Antibodies can be used for both steps, however other agents might also be used, thus ligands for these markers may also be employed to enrich for cells carrying them, or lacking them.

The antibodies or ligands may be attached to a solid support to allow for a crude separation. The separation techniques preferably maximise the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS. Methods for performing FACS will be apparent to the skilled artisan.

Antibodies against each of the markers described herein are commercially available (e.g., monoclonal antibodies against STRO-1 are commercially available from R&D Systems, USA), available from ATCC or other depositary organization and/or can be produced using art recognized techniques.

It is preferred that the method for isolating STRO-1$^{bright}$ cells, for example, comprises a first step being a solid phase sorting step utilising for example magnetic activated cell sorting (MACS) recognising high level expression of STRO-1. A second sorting step can then follow, should that be desired, to result in a higher level of precursor cell expression. This second sorting step might involve the use of two or more markers.

The method obtaining STRO-1$^{bright}$ cells might also include the harvesting of a source of the cells before the first enrichment step using known techniques. Thus the tissue will be surgically removed. Cells comprising the source tissue will then be separated into a so called single cells suspension. This separation may be achieved by physical and or enzymatic means.

Once a suitable STRO-1$^{bright}$ cell population has been obtained, it may be cultured or expanded by any suitable means to obtain MEMPs.

In one embodiment, the cells are taken from the subject to be treated, cultured in vitro using standard techniques and used to obtain supernatant or soluble factors or expanded cells for administration to the subject as an autologous or allogeneic composition. In an alternative embodiment, cells of one or more of the established human cell lines are used to obtain the supernatant or soluble factors. In another useful embodiment of the invention, cells of a non-human animal (or if the patient is not a human, from another species) are used to obtain supernatant or soluble factors.

The invention can be practised using cells from any non-human animal species, including but not limited to non-human primate cells, ungulate, canine, feline, lagomorph, rodent, avian, and fish cells. Primate cells with which the invention may be performed include but are not limited to cells of chimpanzees, baboons, cynomolgus monkeys, and any other New or Old World monkeys. Ungulate cells with which the invention may be performed include but are not limited to cells of bovines, porcines, ovines, caprines, equines, buffalo and bison. Rodent cells with which the invention may be performed include but are not limited to mouse, rat, guinea pig, hamster and gerbil cells. Examples of lagomorph species with which the invention may be performed include domesticated rabbits, jack rabbits, hares, cottontails, snowshoe rabbits, and pikas. Chickens (*Gallus gallus*) are an example of an avian species with which the invention may be performed.

Cells useful for the methods of the invention may be stored before use, or before obtaining the supernatant or soluble factors. Methods and protocols for preserving and storing of eukaryotic cells, and in particular mammalian cells, are known in the art (cf., for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.).

Genetically-Modified Cells

In one embodiment, the STRO-1$^{bright}$ cells and/or progeny cells thereof are genetically modified, e.g., to express and/or secrete a protein of interest, e.g., a protein providing a therapeutic and/or prophylactic benefit, e.g., insulin, glucagon, somatostatin, trypsinogen, chymotrypsinogen, elastase, carboxypeptidase, pancreatic lipase or amylase or a polypeptide associated with or causative of enhanced angiogenesis or a polypeptide associated with differentiation of a cell into a pancreatic cell or a vascular cell.

Methods for genetically modifying a cell will be apparent to the skilled artisan. For example, a nucleic acid that is to be expressed in a cell is operably-linked to a promoter for inducing expression in the cell. For example, the nucleic acid is linked to a promoter operable in a variety of cells of a subject, such as, for example, a viral promoter, e.g., a CMV promoter (e.g., a CMV-IE promoter) or a SV-40 promoter. Additional suitable promoters are known in the art and shall be taken to apply mutatis mutandis to the present embodiment of the invention.

Preferably, the nucleic acid is provided in the form of an expression construct. As used herein, the term "expression construct" refers to a nucleic acid that has the ability to confer expression on a nucleic acid (e.g. a reporter gene and/or a counter-selectable reporter gene) to which it is operably connected, in a cell. Within the context of the present invention, it is to be understood that an expression construct may comprise or be a plasmid, bacteriophage, phagemid, cosmid, virus sub-genomic or genomic fragment, or other nucleic acid capable of maintaining and/or replicating heterologous DNA in an expressible format.

Methods for the construction of a suitable expression construct for performance of the invention will be apparent to the skilled artisan and are described, for example, in Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001). For example, each of the components of the expression construct is amplified from a suitable template nucleic acid using, for example, PCR and subsequently cloned into a suitable expression construct, such as for example, a plasmid or a phagemid.

Vectors suitable for such an expression construct are known in the art and/or described herein. For example, an expression vector suitable for the method of the present invention in a mammalian cell is, for example, a vector of the pcDNA vector suite supplied by Invitrogen, a vector of the pCI vector suite (Promega), a vector of the pCMV vector suite (Clontech), a pM vector (Clontech), a pSI vector (Promega), a VP 16 vector (Clontech) or a vector of the pcDNA vector suite (Invitrogen).

The skilled artisan will be aware of additional vectors and sources of such vectors, such as, for example, Invitrogen Corporation, Clontech or Promega.

Means for introducing the isolated nucleic acid molecule or a gene construct comprising same into a cell for expression are known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

Alternatively, an expression construct of the invention is a viral vector. Suitable viral vectors are known in the art and commercially available. Conventional viral-based systems for the delivery of a nucleic acid and integration of that nucleic acid into a host cell genome include, for example, a retroviral vector, a lentiviral vector or an adeno-associated viral vector. Alternatively, an adenoviral vector is useful for introducing a nucleic acid that remains episomal into a host cell. Viral vectors are an efficient and versatile method of gene transfer in target cells and tissues. Additionally, high transduction efficiencies have been observed in many different cell types and target tissues.

For example, a retroviral vector generally comprises cis-acting long terminal repeats (LTRs) with packaging capacity for up to 6-10 kb of foreign sequence. The minimum cis-acting LTRs are sufficient for replication and packaging of a vector, which is then used to integrate the expression construct into the target cell to provide long term expression. Widely used retroviral vectors include those based upon murine leukemia virus (MuLV), gibbon ape leukemia virus (GaLV), simian immunodeficiency virus (SrV), human immunodeficiency virus (HIV), and combinations thereof (see, e.g., Buchscher et al., *J Virol.* 56:2731-2739 (1992); Johann et al, *J. Virol.* 65:1635-1640 (1992); Sommerfelt et al, *Virol.* 76:58-59 (1990); Wilson et al, *J. Virol.* 63:274-2318 (1989); Miller et al., *J. Virol.* 65:2220-2224 (1991); PCT/US94/05700; Miller and Rosman *BioTechniques* 7:980-990, 1989; Miller, A. D. *Human Gene Therapy* 7:5-14, 1990; Scarpa et al *Virology* 75:849-852, 1991; Burns et al. *Proc. Natl. Acad. Sci USA* 90:8033-8037, 1993).

Various adeno-associated virus (AAV) vector systems have also been developed for nucleic acid delivery. AAV vectors can be readily constructed using techniques known in the art. See, e.g., U.S. Pat. Nos. 5,173,414 and 5,139,941; International Publication Nos. WO 92/01070 and WO 93/03769; Lebkowski et al. *Molec. Cell. Biol.* 5:3988-3996, 1988; Vincent et al. (1990) Vaccines 90 (Cold Spring Harbor Laboratory Press); Carter *Current Opinion in Biotechnology* 5:533-539, 1992; Muzyczka. *Current Topics in Microbiol, and Immunol.* 158:97-129, 1992; Kotin, Human Gene Therapy 5:793-801, 1994; Shelling and Smith *Gene Therapy* 7:165-169, 1994; and Zhou et al. *J Exp. Med.* 179:1867-1875, 1994.

Additional viral vectors useful for delivering an expression construct of the invention include, for example, those derived from the pox family of viruses, such as vaccinia virus and avian poxvirus or an alphavirus or a conjugate virus vector (e.g. that described in Fisher-Hoch et al., *Proc. Natl Acad. Sci. USA* 56:317-321, 1989).

Assaying Therapeutic/Prophylactic Potential of Cells and Soluble Factors

Methods for determining the ability of soluble factors derived from STRO-1$^{bright}$ cells to treat or prevent or delay the onset or progression of GvHD will be apparent to the skilled artisan.

For example, suitable in vitro tests for determining immunosuppressive activity of the soluble factors are described in Example 5 herein.

In another example, efficacy of soluble factors may be assessed in an in vivo model of GvHD as described in Examples 6 and 7 herein.

It will be apparent to the skilled artisan from the foregoing that the present disclosure also provides a method for identifying or isolating a soluble factor for the treatment, prevention or delay of GvHD, the method comprising:
(i) administering a a soluble factor to a test subject suffering from GvHD and assessing progression of GvHD in the subject;
(ii) comparing level of GvHD in the subject at (i) to the level GvHD in a control subject suffering from GvHD to which the soluble factor has not been administered, wherein reduced GvHD in the test subject compared to the control subject indicates that the soluble factor treats, prevents or delays GvHD.

Cellular Compositions

In one embodiment of the present invention STRO-1$^{bright}$ cells and/or progeny cells thereof are administered in the form of a composition. Preferably, such a composition comprises a pharmaceutically acceptable carrier and/or excipient.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for this invention include those conventionally used, e.g., water, saline, aqueous dextrose, lactose, Ringer's solution, a buffered solution, hyaluronan and glycols are preferred liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. Preferably, such a media composition does not induce any adverse effects in a subject to whom it is administered.

Preferred carriers and excipients do not adversely affect the viability of a cell and/or the ability of a cell to reduce, prevent or delay pancreatic dysfunction.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the invention may be produced as a liquid for direct application to the blood stream or into a tissue or a region surrounding or adjacent to a tissue, e.g., by injection.

STRO-1$^{bright}$ cells and/or progeny cells thereof can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of the invention. Preferred scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, e.g., as described by Vacanti, et al. *J. Ped. Surg.* 23:3-9 1988; Cima, et al. *Biotechnol. Bioeng.* 38:145 1991; Vacanti, et al. *Plast. Reconstr. Surg.* 88:753-9 1991; or synthetic polymers such as polyanhydrides, polyorthoesters, and polylactic acid.

In another example, the cells may be administered in a gel scaffold (such as Gelfoam from Upjohn Company).

The cellular compositions useful for the present invention may be administered alone or as admixtures with other cells. Cells that may be administered in conjunction with the compositions of the present invention include, but are not limited to, other multipotent or pluripotent cells or stem cells, or bone marrow cells. The cells of different types may be admixed with a composition of the invention immediately or shortly prior to administration, or they may be co-cultured together for a period of time prior to administration.

Preferably, the composition comprises an effective amount or a therapeutically or prophylactically effective amount of cells. For example, the composition comprises about $1\times10^5$ STRO-1$^{bright}$ cells/kg to about $1\times10^7$ STRO-1$^{bright}$ cells/kg or about $1\times10^6$ STRO-1$^{bright}$ cells/kg to about $5\times10^6$ STRO-1$^{bright}$ cells/kg. The exact amount of cells to be administered is dependent upon a variety of factors, including the age, weight, and sex of the patient, and the extent and severity of the pancreatic dysfunction.

In some embodiments, cells are contained within a chamber that does not permit the cells to exit into a subject's circulation, however that permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors, e.g., implanted in or near a transplanted organ.

In some embodiments of the invention, it may not be necessary or desirable to immunosuppress a patient prior to initiation of therapy with cellular compositions. Accordingly, transplantation with allogeneic, or even xenogeneic, STRO-1$^{bright}$ cells or progeny thereof may be tolerated in some instances.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device. The cells may be encapsulated in a capsule that is permeable to nutrients and oxygen required by the cell and therapeutic factors the cell is yet impermeable to immune humoral factors and cells. Preferably the encapsulant is hypoallergenic, is easily and stably situated in a target tissue, and provides added protection to the implanted structure. These and other means for reducing or eliminating an immune response to the transplanted cells are known in the art. As an alternative, the cells may be genetically modified to reduce their immunogenicity.

Compositions of Soluble Factors

In one embodiment of the present invention, STRO-1$^{bright}$ cell-derived and/or progeny cell-derived supernatant or soluble factors are administered in the form of a composition, e.g., comprising a suitable carrier and/or excipient. Preferably, the carrier or excipient does not adversely affect the biological effect of the soluble factors or supernatant.

In one embodiment, the composition comprises a composition of matter to stabilize a soluble factor or a component of supernatant, e.g., a protease inhibitor. Preferably, the protease inhibitor is not included in an amount sufficient to have an adverse effect on a subject.

Compositions comprising STRO-1$^{bright}$ cell-derived and/or progeny cell-derived supernatant or soluble factors may be prepared as appropriate liquid suspensions, e.g., in culture medium or in a stable carrier or a buffer solution, e.g., phosphate buffered saline. Suitable carriers are described herein above. In another example, suspensions comprising Stro-1$^{bri}$ cell-derived and/or progeny cell-derived supernatant or soluble factors are oily suspensions for injection. Suitable lipophilic solvents or vehicles include fatty oils such as sesame oil; or synthetic fatty acid esters, such as ethyl oleate or triglycerides; or liposomes. Suspensions to be used for injection may also contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Sterile injectable solutions can be prepared by incorporating the supernatant or soluble factors in the required amount in an appropriate solvent with one or a combination of ingredients described above, as required, followed by filtered sterilization.

Generally, dispersions are prepared by incorporating the supernatant or soluble factors into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, the supernatant or soluble factors may be formulated with one or more additional compounds that enhance its solubility.

Other exemplary carriers or excipients are described, for example, in Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.

Therapeutic compositions typically should be sterile and stable under the conditions of manufacture and storage. The composition can be formulated as a solution, microemulsion, liposome, or other ordered structure. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the soluble factors may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

The supernatant or soluble factors may be administered in combination with an appropriate matrix, for instance, to provide slow release of the soluble factors.

Modes of Administration

The STRO-1$^{bright}$ cell-derived supernatant or soluble factors, STRO-1$^{bright}$ cells or progeny thereof may be surgically implanted, injected, delivered (e.g., by way of a catheter or syringe), or otherwise administered directly or indirectly to the site in need of repair or augmentation, e.g., an organ or into the blood system of a subject.

Preferably, the STRO-1$^{bright}$ cell-derived supernatant or soluble factors, STRO-1$^{bright}$ cells or progeny thereof is delivered to the blood stream of a subject. For example, the STRO-1$^{bright}$ cell-derived supernatant or soluble factors, STRO-1$^{bright}$ cells or progeny thereof are delivered parenterally. Exemplary routes of parenteral administration include, but are not limited to, intravenous, intramuscular, subcutaneous, intra-arterial, intraperitoneal, intraventricular, intracerebroventricular, intrathecal. Preferably, the STRO-1$^{bright}$ cell-derived supernatant or soluble factors, STRO-1$^{bright}$ cells or progeny thereof are delivered intra-arterially, into an aorta, into an atrium or ventricle of the heart or into a blood vessel connected to a pancreas, e.g., an abdominal aorta, a superior mesenteric artery, a pancreaticoduodenal artery or a splenic artery.

In the case of cell delivery to an atrium or ventricle of the heart, it is preferred that cells are administered to the left atrium or ventricle to avoid complications that may arise from rapid delivery of cells to the lungs.

Preferably, the STRO-1$^{bright}$ cell-derived supernatant or soluble factors, STRO-1$^{bright}$ cells or progeny thereof are injected into the site of delivery, e.g., using a syringe or through a catheter or a central line.

Selecting an administration regimen for a therapeutic formulation depends on several factors, including the serum or tissue turnover rate of the entity, the level of symptoms, and the immunogenicity of the entity. Preferably, an administration regimen maximizes the amount of therapeutic compound delivered to the patient consistent with an acceptable level of side effects. Accordingly, the amount of formulation delivered depends in part on the particular entity and the severity of the condition being treated.

In one embodiment, STRO-1$^{bright}$ cell-derived supernatant or soluble factors, STRO-1$^{bright}$ cells or progeny thereof are delivered as a single bolus dose. Alternatively, STRO-1$^{bright}$ cell-derived supernatant or soluble factors, STRO- 1$^{bright}$ cells or progeny thereof are administered by continuous infusion, or by doses at intervals of, e.g., one day, one week, or 1-7 times per week. A preferred dose protocol is one involving the maximal dose or dose frequency that avoids significant undesirable side effects. A total weekly dose depends on the type and activity of the compound being used. Determination of the appropriate dose is made by a clinician, e.g., using parameters or factors known or suspected in the art to affect treatment or predicted to affect treatment. Generally, the dose begins with an amount somewhat less than the optimum dose and is increased by small increments thereafter until the desired or optimum effect is achieved relative to any negative side effects. Important diagnostic measures include those of symptoms of diabetes.

EXAMPLES

Example 1: MSC Preparation

MSCs are generated de novo from bone marrow as described in U.S. Pat. No. 5,837,539. Approximately 80-100 ml of marrow was aspirated into sterile heparin-containing syringes and taken to the MDACC Cell Therapy Laboratory for MSC generation. The bone marrow mononuclear cells were isolated using ficoll-hypaque and placed into two T175 flask with 50 ml per flask of MSC expansion medium which includes alpha modified MEM (αMEM) containing gentamycin, glutamine (2 mM) and 20% (v/v) fetal bovine serum (FBS) (Hyclone).

The cells were cultured for 2-3 days in 37° C., 5% $CO_2$ at which time the non-adherent cells were removed; the remaining adherent cells were continually cultured until the cell confluence reached 70% or higher (7-10 days), and then the cells were trypsinized and replaced in six T175 flasks with MSC expansion medium (50 ml of medium per flask). As described in Table 5 of U.S. Pat. No. 5,837,539, MSCs isolated and expanded in this manner are STRO-1 negative.

Example 2: Immunoselection of MPCs by Selection of STRO-3+ Cells

Bone marrow (BM) is harvested from healthy normal adult volunteers (20-35 years old), in accordance with procedures approved by the Institutional Ethics Committee of the Royal Adelaide Hospital. Briefly, 40 ml of BM is aspirated from the posterior iliac crest into lithium-heparin anticoagulant-containing tubes.

BMMNC are prepared by density gradient separation using Lymphoprep™ (Nycomed Pharma, Oslo, Norway) as previously described (Zannettino, A. C. et al. (1998) Blood 92: 2613-2628). Following centrifugation at 400×g for 30 minutes at 4° C., the buffy layer is removed with a transfer pipette and washed three times in "HHF", composed of Hank's balanced salt solution (HBSS; Life Technologies, Gaithersburg, Md.), containing 5% fetal calf serum (FCS, CSL Limited, Victoria, Australia).

STRO-3+ (or TNAP+) cells were subsequently isolated by magnetic activated cell sorting as previously described (Gronthos et al. (2003) Journal of Cell Science 116: 1827-1835; Gronthos, S. and Simmons, P. J. (1995) Blood 85: 929-940). Briefly, approximately $1-3 \times 10^8$ BMMNC are incubated in blocking buffer, consisting of 10% (v/v) normal rabbit serum in HHF for 20 minutes on ice. The cells are incubated with 200 μl of a 10 μg/ml solution of STRO-3 mAb in blocking buffer for 1 hour on ice. The cells are subsequently washed twice in HHF by centrifugation at 400×g. A 1/50 dilution of goat anti-mouse γ-biotin (Southern Biotechnology Associates, Birmingham, UK) in HHF buffer is added and the cells incubated for 1 hour on ice. Cells are washed twice in MACS buffer ($Ca^{2+}$- and $Mn^{2+}$-free PBS supplemented with 1% BSA, 5 mM EDTA and 0.01% sodium azide) as above and resuspended in a final volume of 0.9 ml MACS buffer.

One hundred μl streptavidin microbeads (Miltenyi Biotec; Bergisch Gladbach, Germany) are added to the cell suspension and incubated on ice for 15 minutes. The cell suspension is washed twice and resuspended in 0.5 ml of MACS buffer and subsequently loaded onto a mini MACS column (MS Columns, Miltenyi Biotec), and washed three times with 0.5 ml MACS buffer to retrieve the cells which did not bind the STRO-3 mAb (deposited on 19 Dec. 2005 with American Type Culture Collection (ATCC) under accession number PTA-7282—see International Publication No. WO 2006/108229). After addition of a further 1 ml MACS buffer, the column is removed from the magnet and the TNAP+ cells are isolated by positive pressure. An aliquot of cells from each fraction can be stained with streptavidin-FITC and the purity assessed by flow cytometry.

Example 3: Cells Selected by STRO-3 mAb are STRO-1$^{bright}$ Cells

Experiments were designed to confirm the potential of using STRO-3 mAb as a single reagent for isolating cells STRO-1$^{bright}$ cells.

Given that STRO-3 (IgG1) is a different isotype to that of STRO-1 (IgM), the ability of STRO-3 to identify clonogenic CFU-F was assessed by two-colour FACS analysis based on its co-expression with STRO-1+ cells isolated using the MACS procedure (FIG. 1). The dot plot histogram represents $5 \times 10^4$ events collected as listmode data. The vertical and horizontal lines were set to the reactivity levels of <1.0% mean fluorescence obtained with the isotype-matched control antibodies, 1B5 (IgG) and 1A6.12 (IgM) treated under the same conditions. The results demonstrate that a minor population of STRO-1$^{bright}$ cells co-expressed TNAP (upper right quadrant) while the remaining STRO-1+ cells failed to react with the STRO-3 mAb. Cells isolated by FACS from all four quadrants were subsequently assayed for the incidence of CFU-F (Table 1).

TABLE 1

Enrichment of human bone marrow cells by dual-colour FACS analysis based on the co-expression of the cell surface markers STRO-1 and TNAP (refer to FIG. 1). FACS sorted cells were cultured under standard clonogenic conditions in alpha MEM supplemented with 20% FCS. The data represents the mean number of day 14 colony-forming cells (CFU-F) per $10^5$ cells plated ± SE (n = 3 different bone marrow aspirates). These data suggest that human MPC are exclusively restricted to the TNAP positive fraction of BM which co-express the STRO-1 antigen brightly.

| Bone Marrow Fraction | Frequency of CFU-F/$10^5$ Cells | Enrichment (Fold Increase) |
| --- | --- | --- |
| Unfractionated BMMNC | 11.0 ± 2.2 | 1.0 |
| TNAP+/STRO-1$^{bright}$ | 4,511 ± 185 | 410 |
| TNAP+/STRO-1l$^{dull}$ | 0.0 | 0.0 |

Figure 2:
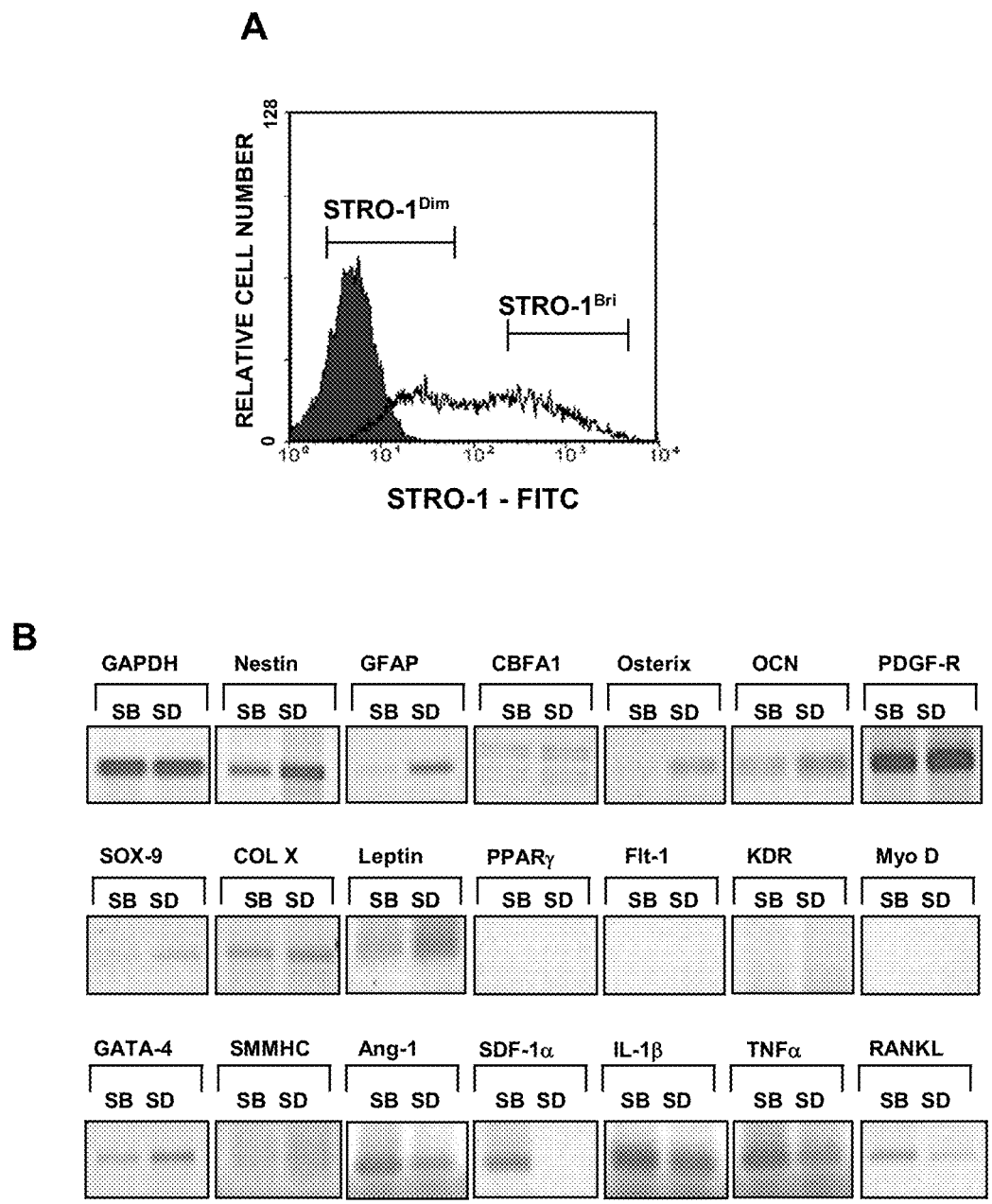
FIG. 2. Gene expression profile of STRO-1$^{bright}$ or STRO-1$^{dim}$ progeny of cultured and expanded STRO-1$^{bright}$ MPC. Single cell suspensions of ex vivo expanded bone marrow MPC were prepared by trypsin/EDTA treatment. Cells were stained with the STRO-1 antibody which was subsequently revealed by incubation with goat-anti murine IgM-fluorescein isothiocyanate. Total cellular RNA was prepared from purified populations of STRO-1$^{dim}$ or STRO-1$^{bright}$ expressing cells, following fluorescence activated cell sorting (A). Using RNAzolB extraction method, and standard procedures, total RNA was isolated from each subpopulation and used as a template for cDNA synthesis. The expression of various transcripts was assessed by PCR amplification, using a standard protocol as described previously (Gronthos et al. J Cell Sci. 116:1827-1835, 2003). Primers sets used in this study are shown in Table 2. Following amplification, each reaction mixture was analysed by 1.5% agarose gel electrophoresis, and visualised by ethidium bromide staining (B). Relative gene expression for each cell marker was assessed with reference to the expression of the housekeeping gene, GAPDH, using ImageQant software (C).
Figure 2:
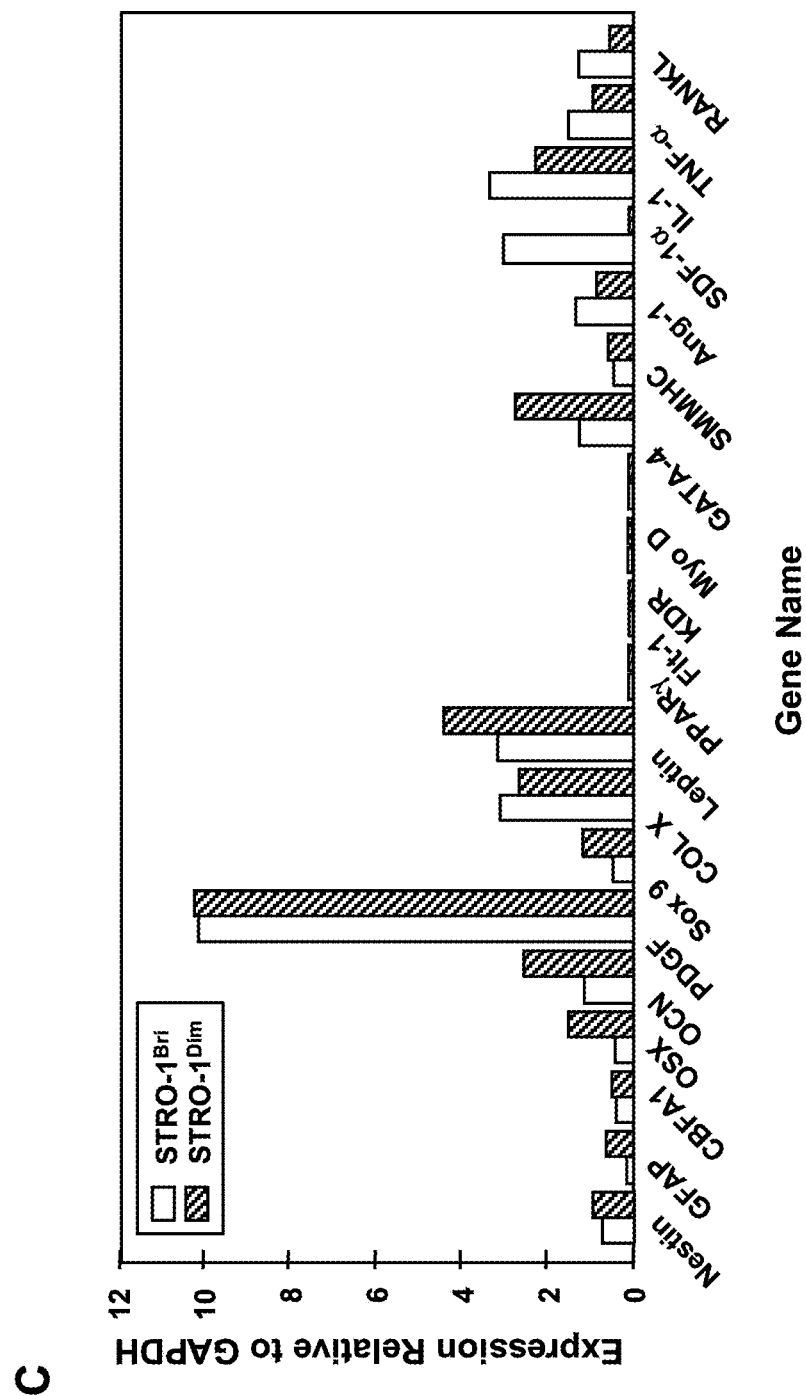

Example 4: Relative Gene and Surface Protein Expression of STRO-1$^{dull}$ and Stro-1$^{bright}$ Cells In the first series of experiments, semi-quantitative RT-PCR analysis was employed to examine the gene expression profile of various lineage-associated genes expressed by STRO-1$^{dull}$ or STRO-1$^{bright}$ populations, isolated by fluorescence activated cell sorting (FIG. 2A). In the second series of experiments, flow cytometry and mean channel fluorescence analysis was employed to examine the surface protein xpression profile of various lineage-associated proteins expressed by STRO-1$^{dull}$ or STRO-1$^{bright}$ populations, isolated by fluorescence activated cell sorting.

Total cellular RNA was prepared from either 2×10$^6$ STRO-1$^{bright}$ or STRO-1$^{dull}$ sorted primary cells, chondrocyte pellets and other induced cultures and lysed using RNAzolB extraction method (Biotecx Lab. Inc., Houston, Tex.), according to the manufacturer's recommendations. RNA isolated from each subpopulation was then used as a template for cDNA synthesis, prepared using a First-strand cDNA synthesis kit (Pharmacia Biotech, Uppsala, Sweden). The expression of various transcripts was assessed by PCR amplification, using a standard protocol as described previously (Gronthos et al., J. Bone and Min. Res. 14:48-57, 1999). Primer sets used in this study are shown in Table 2. Following amplification, each reaction mixture was analysed by 1.5% agarose gel electrophoresis, and visualised by ethidium bromide staining. RNA integrity was assessed by the expression of GAPDH.

Relative gene expression for each cell marker was assessed with reference to the expression of the housekeeping gene, GAPDH, using ImageQant software (FIG. 2B, C). In addition, dual-colour flow cytometric analysis was used to examine the protein expression profile of ex vivo expanded MPC based on their expression of a wider range of cell lineage-associated markers in combination with the STRO-1 antibody. A summary of the general phenotype based on the gene and protein expression of STRO-1$^{dull}$ and STRO-1$^{bright}$ cultured cells is presented in Table 3. The data indicate that ex vivo expanded STRO-1$^{bright}$ MPC exhibit differentially higher expression of markers associated with perivascular cells, including angiopoietin-1, VCAM-1, SDF-1, IL-1$_\beta$, TNF$\alpha$, and RANKL. Comparisons between the protein and gene expression profiles of STRO-1$^{dull}$ and STRO-1$^{bright}$ cultured cells are summarised in Tables 3 and 4.

Subtractive hybridization studies were also performed in order to identify genes uniquely expressed by STRO-1$^{bright}$ cells. Briefly, STRO-1$^{dull}$ and STRO-1$^{bright}$ were isolated as described above (see FIG. 3A). Total RNA was prepared from STRO-1$^{dull}$ and STRO-1$^{bright}$ cells pooled from 5 different marrow samples using the RNA STAT-60 system (TEL-TEST). First-strand synthesize was performed using the SMART cDNA synthesis kit (Clontech Laboratories). The resultant mRNA/single-stranded cDNA hybrid was amplified by long-distance PCR (Advantage 2 PCR kit; Clontech) using specific primer sites at the 3' and 5' prime ends formed during the initial RT process according to the manufacturer's specifications. Following RsaI digestion of the STRO-1$^{bright}$ cDNA, 2 aliquots were used to ligate different specific adaptor oligonucleotides using the Clontech PCR-Select cDNA Subtraction Kit. Two rounds of subtractive hybridization were performed using STRO-1$^{bright}$ (tester) and STRO-1$^{dull}$ (driver) cDNA, and vice versa, according to the manufacturer's protocol. This procedure was also performed in reverse using STRO-1$^{dull}$ tester cDNA hybridized against STRO-1$^{bright}$ driver cDNA.

Figure 3:
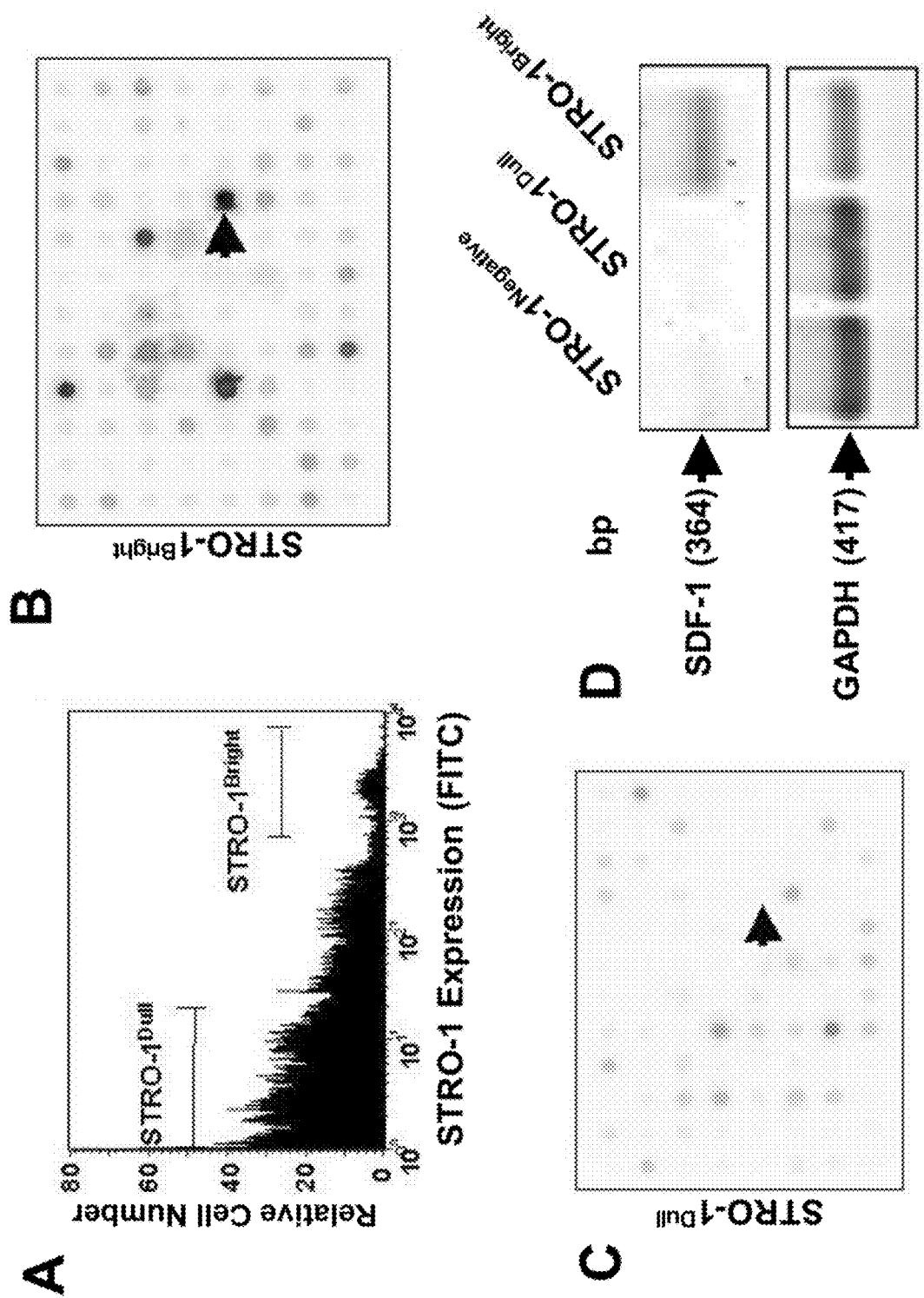
FIG. 3. STRO-1$^{bright}$ progeny of cultured and expanded STRO-1+ MPC express high levels of SDF-1, STRO-1$^{dim}$ progeny do not. (A) MACS-isolated preparations of STRO-1+ BMMNCs were partitioned into different STRO-1 subsets according to the regions, STRO-1$^{bright}$ and STRO-1$^{dim/dull}$ using FACS. Total RNA was prepared from each STRO-1 subpopulation and used to construct a STRO-1$^{bright}$ subtraction hybridization library (B-C). Replicate nitrocellulose filters, which have been blotted with representative PCR products amplified from bacterial clones transformed with STRO-1$^{bright}$ subtracted cDNA. The filters were then probed with either [$^{32}$P] deoxycytidine triphosphate (dCTP)-labeled STRO-1$^{bright}$ (B) or STRO-1$^{dim/dull}$ (C) subtracted cDNA. The arrows indicate differential expression of 1 clone containing a cDNA fragment corresponding to human SDF-1. (D) Reverse transcriptase (RT)-PCR analysis demonstrating the relative expression of SDF-1 and glyceraldehyde-3-phosphate dehydrogenase (GAPDH) transcripts in total RNA prepared from freshly MACS/FACS-isolated BMMNC STRO-1 populations prior to culture. bp indicates base pair.

To identify genes uniquely expressed by STRO-1$^{bright}$ population, STRO-1$^{bright}$-subtracted cDNA was used to construct replicate low-density microarray filters comprising 200 randomly selected bacterial clones transformed with the STRO-1$^{bright}$ subtracted cDNAs ligated into a T/A cloning vector. The microarrays were subsequently probed with either [$^{32}$P] dCTP-labeled STRO-1$^{bright}$ or STRO-1$^{dull}$ subtracted cDNA (FIG. 3B-C). Differential screening identified a total of 44 clones, which were highly differentially expressed between the STRO-1$^{dull}$ and STRO-1$^{bright}$ subpopulations. DNA sequencing of all the differentially expressed clones revealed that only 1 clone was representative of a known stromal cell mitogen; namely, platelet-derived growth factor (PDGF) (Gronthos and Simmons, Blood. 85: 929-940, 1995). Interestingly, 6 of the 44 clones were found to contain DNA inserts corresponding to the chemokine, stromal-derived factor-1 (SDF-1). The high abundance of SDF-1 transcripts in human STRO-1$^{bright}$ cells was confirmed by semiquantitative RT-PCR of total RNA prepared from freshly sorted STRO-1$^{bright}$, STRO-1$^{dull}$, and STRO-1$^{negative}$ bone marrow subpopulations (FIG. 3D and Table 3).

TABLE 2

RT-PCR primers and conditions for the specific amplification of human mRNA

| Target Gene | Sense/Antisense (5'-3') Primer Sequences | Product Size | SEQ ID |
|---|---|---|---|
| GAPDH | CACTGACACGTTGGCAGTGG/<br>CATGGAGAAGGCTGGGGCTC | 417 | SEQ ID NO: 1<br>SEQ ID NO: 2 |
| SFD-1 | GAGACCCGCGCTCGTCCGCC/<br>GCTGGACTCCTACTGTAAGGG | 364 | SEQ ID NO: 3<br>SEQ ID NO: 4 |
| IL-1β | AGGAAGATGCTGGTTCCCTCTC/<br>CAGTTCAGTGATCGTACAGGTGC | 151 | SEQ ID NO: 5<br>SEQ ID NO: 6 |
| FLT-1 | TCACTATGGAAGATCTGATTTCTTACAGT/<br>GGTATAAATACACATGTGCTTCTAG | 380 | SEQ ID NO: 7<br>SEQ ID NO: 8 |
| TNF-α | TCAGATCATCTTCTCGAACC/<br>CAGATAGATGGGCTCATACC | 361 | SEQ ID NO: 9<br>SEQ ID NO: 10 |
| KDR | TATAGATGGTGTAACCCGGA/<br>TTTGTCACTGAGACAGCTTGG | 450 | SEQ ID NO: 11<br>SEQ ID NO: 12 |
| RANKL | AACAGGCCTTTCAAGGAGCTG/<br>TAAGGAGGGGTTGGAGACCTCG | 538 | SEQ ID NO: 13<br>SEQ ID NO: 14 |

TABLE 2-continued

RT-PCR primers and conditions for the specific amplification of human mRNA

| Target Gene | Sense/Antisense (5'-3') Primer Sequences | Product Size | SEQ ID |
|---|---|---|---|
| Leptin | ATGCATTGGGAACCCTGTGC/<br>GCACCCAGGGCTGAGGTCCA | 492 | SEQ ID NO: 15<br>SEQ ID NO: 16 |
| CBFA-1 | GTGGACGAGGCAAGAGTTTCA/<br>TGGCAGGTAGGTGTGGTAGTG | 632 | SEQ ID NO: 17<br>SEQ ID NO: 18 |
| PPARγ2 | AACTGCGGGGAAACTTGGGAGATTCTCC/<br>AATAATAAGGTGGAGATGCAGGCTCC | 341 | SEQ ID NO: 19<br>SEQ ID NO: 20 |
| OCN | ATGAGAGCCCTCACACTCCTC/<br>CGTAGAAGCGCCGATAGGC | 289 | SEQ ID NO: 21<br>SEQ ID NO: 22 |
| MyoD | AAGCGCCATCTCTTGAGGTA/<br>GCGAGAAACGTGAACCTAGC | 270 | SEQ ID NO: 23<br>SEQ ID NO: 24 |
| SMMHC | CTGGGCAACGTAGTAAAACC/<br>TATAGCTCATTGCAGCCTCG | 150 | SEQ ID NO: 25<br>SEQ ID NO: 26 |
| GFAP | CTGTTGCCAGAGATGGAGGTT/<br>TCATCGCTCAGGAGGTCCTT | 370 | SEQ ID NO: 27<br>SEQ ID NO: 28 |
| Nestin | GGCAGCGTTGGAACAGAGGTTGGA/<br>CTCTAAACTGGAGTGGTCAGGGCT | 460 | SEQ ID NO: 29<br>SEQ ID NO: 30 |
| SOX9 | CTCTGCCTGTTTGGACTTTGT/<br>CCTTTGCTTGCCTTTTACCTC | 598 | SEQ ID NO: 31<br>SEQ ID NO: 32 |
| Collagen type X | AGCCAGGGTTGCCAGGACCA/<br>TTTTCCCACTCCAGGAGGGC | 387 | SEQ ID NO: 33<br>SEQ ID NO: 34 |
| Aggrecan | CACTGTTACCGCCACTTCCC/<br>ACCAGCGGAAGTCCCCTTCG | 184 | SEQ ID NO: 35<br>SEQ ID NO: 36 |

TABLE 3

Summary of the Relative Gene Expression in STRO-1$^{Bright}$ and STRO-1$^{Dull}$ populations. A list of genes which displayed measurable and differential expression between the STRO-1$^{Bright}$ and STRO-1$^{Dull}$ populations as determined by reverse transcription-PCR are presented. Values represent the relative gene expression with reference to the house-keeping gene, GAPDH.

| Tissue | Marker | Gene Expression relative to GAPDH | |
|---|---|---|---|
| | | STRO-1$^{Bright}$ | STRO-1$^{Dull}$ |
| Neurons | GFAP (Glial Fibrillary Acidic Protein) | 0.1 | 0.7 |
| Bone | OCN (Osteocalcin) | 1.1 | 2.5 |
| | OSX (Osterix) | 0.4 | 1.3 |
| | CBFA-1 (Core Factor Binding Protein-1) | 0.3 | 0.6 |
| Immuno-regulatory | RANKL (Receptor Activator of Nuclear Factor κ B) | 1.6 | 0.3 |
| | SDF-1-alpha (Stromal Derived factor-1-alpha) | 3.2 | 0.1 |
| Fat | Leptin | 3.1 | 4.2 |
| Cardio-myocytes | GATA-4 | 1.1 | 2.9 |
| Endothelial cells | Ang-1 (Angiopoietin-1) | 1.5 | 0.8 |
| Chondrocytes | Sox 9 | 0.3 | 1.1 |
| | COL X (Collagen X) | 3.5 | 2.8 |
| Pro-inflammatory Cytokines | TNF-alpha (Tumour necrosis alpha) | 1.7 | 0.9 |

To correlate protein surface expression with density of STRO-1 expression, single cell suspensions of ex vivo expanded cells derived bone marrow MPC were prepared by trypsin/EDTA detachment and subsequently incubated with the STRO-1 antibody in combination with antibodies identifying a wide range of cell lineage-associated markers. STRO-1 was identified using a goat anti-murine IgM-fluorescein isothiocyanate while all other markers were identified using either a goat anti-mouse or anti-rabbit IgG-phycoerythrin. For those antibodies identifying intracellular antigens, cell preparations were first labelled with the STRO-1 antibody, fixed with cold 70% ethanol to permeabilize the cellular membrane and then incubated with intracellular antigen-specific antibodies. Isotype matched control antibodies were used under identical conditions. Dual-colour flow cytometric analysis was performed using a COULTER EPICS flow cytometer and list mode data collected. The dot plots represent 5,000 listmode events indicating the level of fluorescence intensity for each lineage cell marker (y-axis) and STRO-1 (x-axis). The vertical and horizontal quadrants were established with reference to the isotype matched negative control antibodies.

TABLE 4

Summary of the Relative Protein Expression in STRO-1$^{Bright}$ and STRO-1$^{Dull}$ populations. A list of proteins which displayed differential expression between the STRO-1$^{Bright}$ and STRO-1$^{Dull}$ populations as determined by flow cytometry are presented. Values represent the relative mean fluorescence intensity of staining.

| Tissue | Marker | Mean Fluorescence Intensity | |
|---|---|---|---|
| | | STRO-1$^{Bright}$ | STRO-1$^{Dull}$ |
| Neurons | Neurofilament | 1.7 | 20.5 |
| Bone | ALK PHOS (Alkaline Phophatase) | 5.7 | 44.5 |
| Immuno-regulatory | RANKL (Receptor Activator of Nuclear Factor κ B) | 658.5 | 31.0 |
| Epithelial Cells | CytoKeratin 10 + 13 | 1.2 | 23.3 |
| | Cytokeratin 14 | 1.8 | 8.8 |
| Smooth Muscle | α-SMA (Alpha Smooth Muscle Actin) | 318.0 | 286.0 |
| Chondrocytes | Byglycan | 84.4 | 65.9 |
| Basal Fibroblast | Tenascin C | 22.2 | 6.9 |
| Cardiomyocyte | Troponin C | 2.5 | 15.0 |

These results show that SDF-1alpha and RANKL are highly expressed by STRO-1$^{bright}$ cells. This is important because both of these proteins are known to be involved in up-regulation of CD4+ CD25+ regulatory T cells which confer protection against immune disorders such as GVHD (Loser et al., Nature Medicine 12:1372-1379, 2006; Hess, Biol. Blood Marrow Transplant, 12 (1 Suppl 2):13-21, 2006; and Meiron et al., J. Exp. Medicine 205:2643-2655, 2008).

Example 5: In Vitro Immunosuppressive Activity

To assess immunosuppressive activity of culture-expanded STRO-1$^{bright}$ cells (MPC(B)), we used CD3/CD28 stimulation as a read-out. Results were compared to a population of culture-expanded, bone marrow-derived STRO-1 negative cells isolated as in Example 1 (MSC(A)). Human peripheral blood mononuclear cells (PBMC) were stimulated with CD3/CD28 coated beads in the presence of 4 escalating concentrations of MSC and MPC preparations. The proliferation of T cells was measured by 3H-Tdr incorporation.

MSC (A) and STRO-1$^{bright}$ MPCs (B) were tested for their ability to suppress the response of human peripheral blood mononuclear cells (PBMC) to CD3/CD28 stimulation. MSC and MPC or commercially-purchased control human MSC (Lonza) were added at different ratios to the cultures of PBMC. After 3 days, 3H-Tdr was added for 18 hours and the cultures then harvested.

Figure 4:
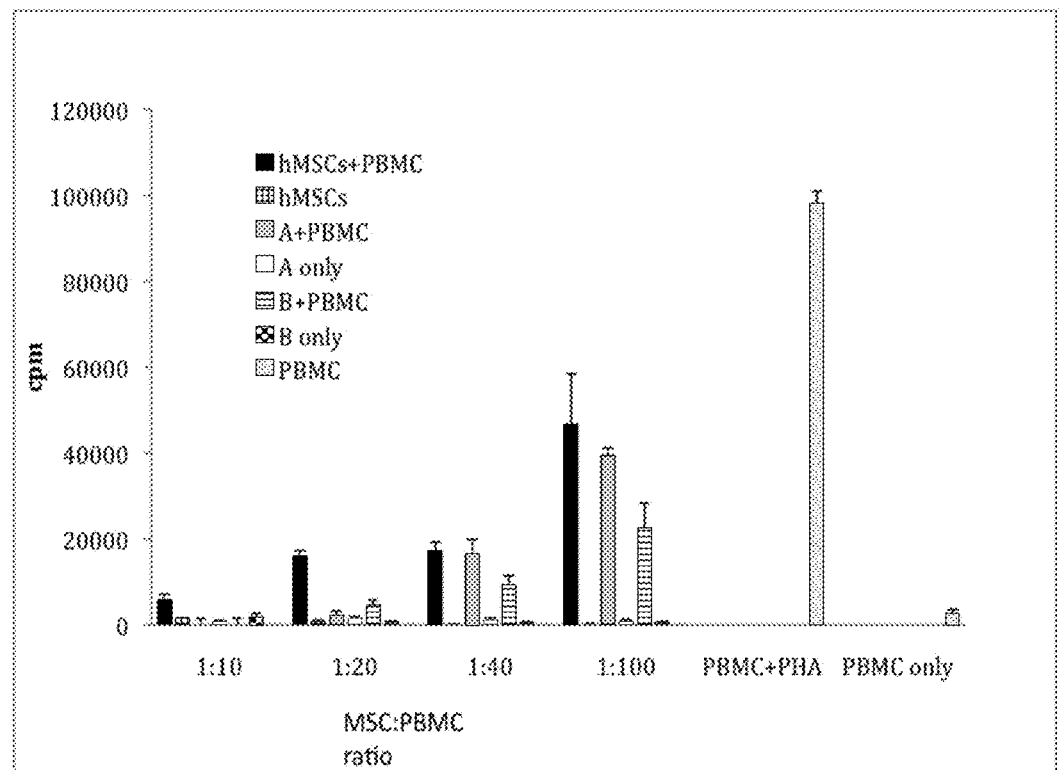
FIG. 4. Comparative efficiency of STRO-1 negative MSC (preparation A) and STRO-1$^{bright}$ MPC (preparation B) for inhibition of T cell proliferation. PBMC were stimulated with CD3/CD28 coated beads for 4 days in the absence or presence of preparations A or B. T cell proliferation was measured by $^3$H-Tdr incorporation as counts per minute (cpm).
Figure 5:
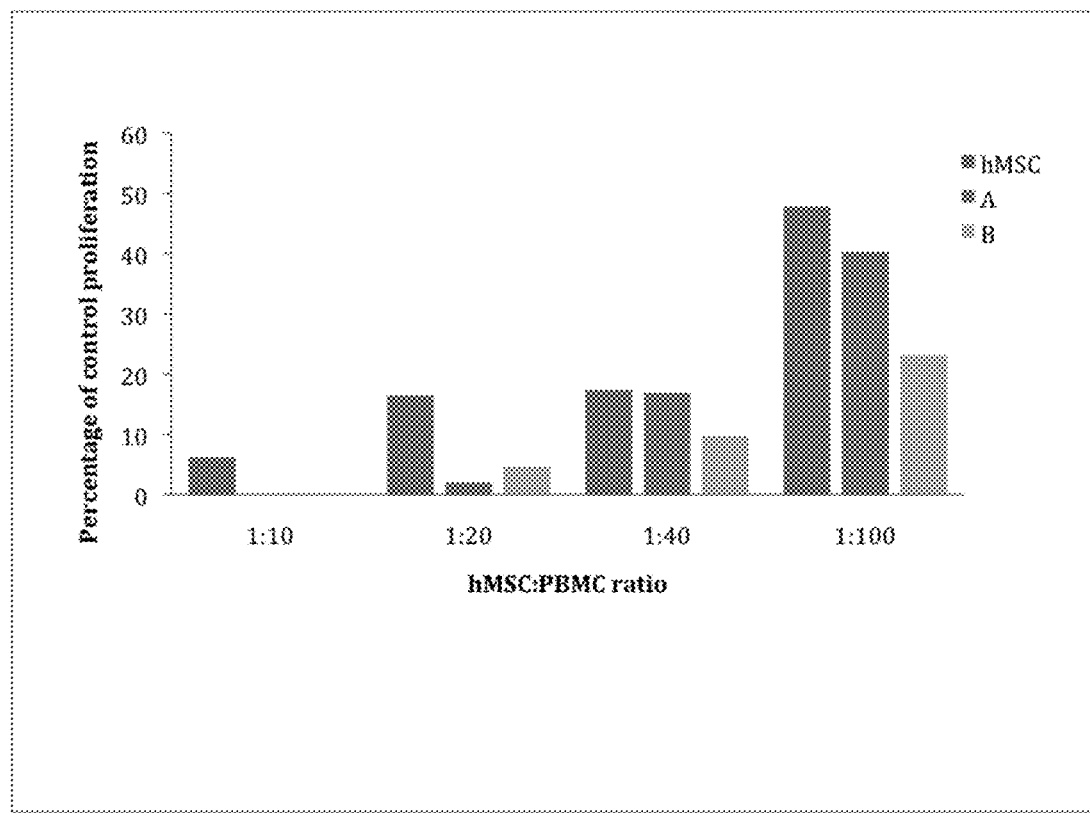
FIG. 5. Comparative efficiency of STRO-1 negative MSC (preparation A) and STRO-1$^{bright}$ MPC (preparation B) for inhibition of T cell proliferation. PBMC were stimulated with CD3/CD28 coated beads for 4 days in the presence of different concentrations of preparations A or B. T cell proliferation in the various cultures were was measured by $^3$H-Tdr incorporation and reported as percentage of the control T cell proliferation in which PBMC were stimulated in the absence of MSC.

PBMC proliferation in response to CD3/CD28 was inhibited in a dose dependent fashion by all preparations. However, preparation B was clearly superior to the effect produced by preparation A as well as control hMSC (FIG. 4). At a 1:100 MSC:PBMC ratio, MPC B still inhibited 70% of control T cell proliferation, whilst control commercially-purchased MSC (Lonza) and MSC A produced a 50% and 60% inhibition, respectively (FIG. 5).

Example 6: Induction and Treatment of GvHD

The in vivo immunosuppressive activity of STRO-1$^{bright}$ cells (MPC(B)) was investigated using a model of graft-versus-host disease (GvHD) based on a donor recipient pair mismatched for multiple minor histocompatibility loci. T-cell depleted bone marrow mononuclear cells (BMMC) (5×10$^6$) and splenocytes (30×10$^6$) from B10.D2 (H2d) donors were injected intravenously into lethally irradiated (750 cGy) BALB/c (H2d) recipient mice. In this situation the splenic lymphocytes from B10.D2 recognise and attack BALB/c recipient tissues and produce weight loss, fibrosis and hair loss. The disease was monitored using the conventional scoring system by weighing the animals and assessing skin manifestations from week 4-5 after the transplant. As a comparison, immunosuppressive activity of bone marrow-derived STRO-1 negative cells isolated as in Example 1 (MSC(A)) was evaluated.

Whereas a positive control group of mice did not receive any further treatment, the experimental groups were injected intravenously with MSCs (A) or STRO-1$^{bright}$ MPCs (B) at a dose of 2×10$^6$, 1×10$^6$, or 0.3×10$^6$/mouse from week 4 every week for 3 times. Mice were monitored twice a week. Each group contained eight mice.

Example 7: Effects of MSCs and MPCs on the Development of GvHD

Figure 6:
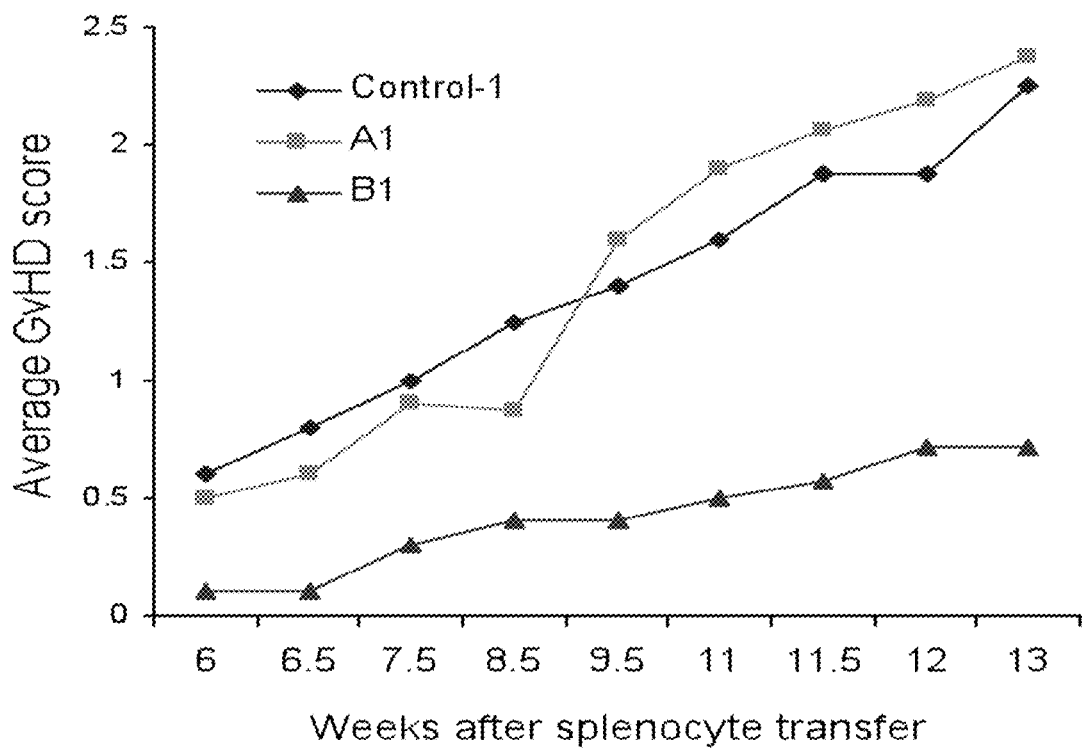
FIG. 6. Comparative effects of STRO-1 negative MSC (preparation A) and STRO-1$^{bright}$ MPC (preparation B) on GvHD. T-cell depleted bone marrow mononuclear cells (BMMC) (5×$10^6$) and splenocytes (30×$10^6$) from B10.D2 (H2d) donors were injected intravenously into lethally irradiated (750 cGy) BALB/c (H2d) recipient mice. After 4 weeks, recipient mice were injected with 1×$10^6$ MSC (preparation A1) or MPC (preparation B1) per mouse or received no further treatment (Control). Eight mice per group were injected. Mice were assessed at weekly interval. Time refer to number of weeks.

Mice received 1 or 2×10$^6$ MSC A (A1 and A2), 1 or 2×10$^6$ MPC B (B1 and B2). The kinetics of disease in the absence or presence of MSC treatment are reported in FIG. 6. Following the infusion of 1×10$^6$ cells, there was a clear difference between the effects of B and A. Whilst mice receiving preparation A did not exhibit any substantial difference from those receiving no cells, the group injected with preparation B showed a dramatic beneficial effect on the severity of the disease. Thirteen weeks after the transplant, mice which had received B1 had an average GvHD score of 0.5 as compared to 2.3 in the other groups.

Figure 7:
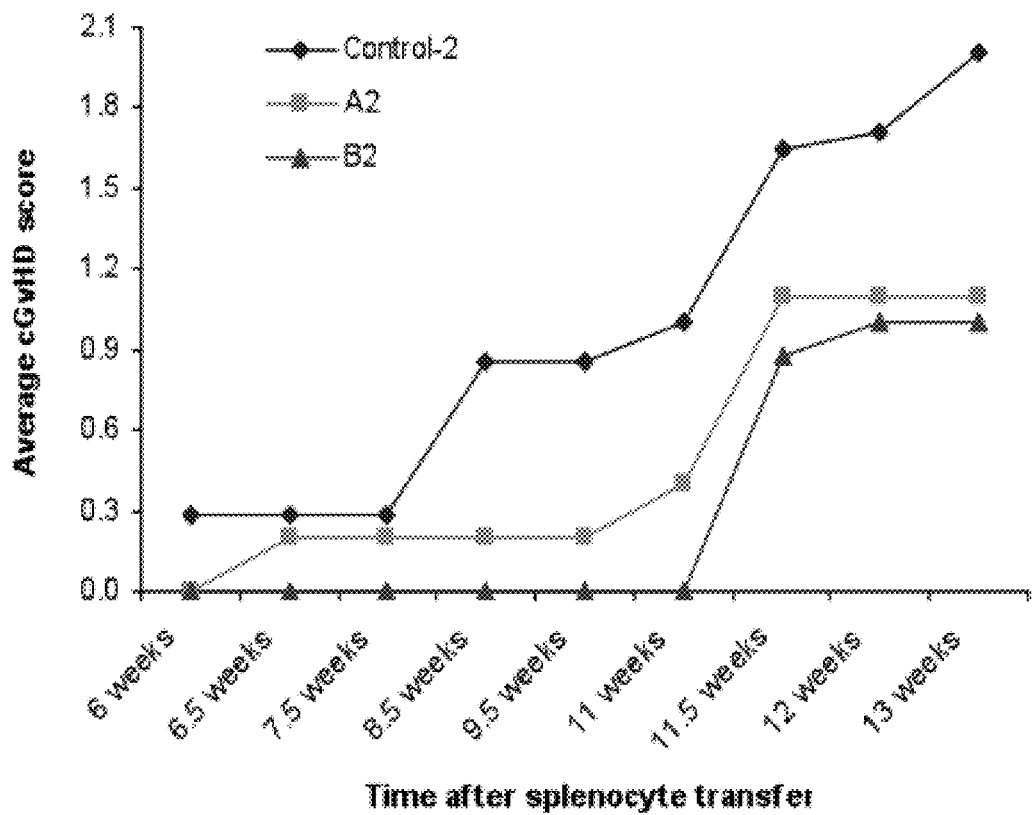
FIG. 7. Comparative effects of STRO-1 negative MSC (preparation A) and STRO-1$^{bright}$ MPC (preparation B) on GvHD. T-cell depleted bone marrow mononuclear cells (BMMC) ($5 \times 10^6$) and splenocytes ($30 \times 10^6$) from B10.D2 (H2d) donors were injected intravenously into lethally irradiated (750 cGy) BALB/c (H2d) recipient mice. After 4 weeks, recipient mice were injected with 1 or $2 \times 10^6$ cells of preparations A or B (A1, A2, B1, B2) or received no further treatment (Ctr). Eight mice per group were injected.
Figure 8:
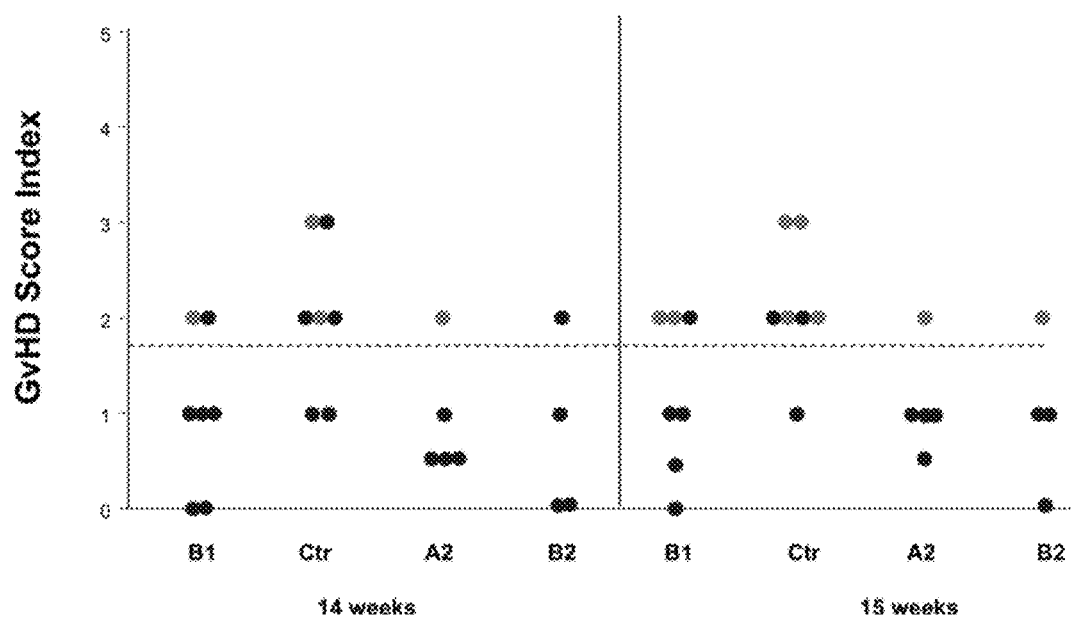
FIG. 8. Comparative effects of high-dose STRO-1 negative MSC (preparation A) and STRO-1$^{bright}$ MPC (preparation B) on GvHD. T-cell depleted bone marrow mononuclear cells (BMMC) ($5 \times 10^6$) and splenocytes ($30 \times 10^6$) from B10.D2 (H2d) donors were injected intravenously into lethally irradiated (750 cGy) BALB/c (H2d) recipient mice. After 4 weeks, recipient mice were injected with $2 \times 10^6$ cells of preparations A or B (A2, B2) or received no further treatment (Control 2). Eight mice per group were injected but 4 and 3 mice died soon after the injection in groups B2 and A2, respectively.

We then investigated whether the anti-GvHD effect was dose dependent. Therefore a group of mice was injected with a higher dose (2×10$^6$ per mouse) and one with a lower dose (0.3×10$^6$ per mouse) of A or B according to the same modalities described for the previous dose. FIG. 7 reports the effects of the highest dose. The therapeutic effect of high dose MPC (B2) was superior relative to A2, with no GvHD seen at all for the first 11 weeks in this group. At 14 and 15 weeks, the consequences of GvHD per mouse was even more dramatic (FIG. 8) with no mice at all surviving in the A1 group.

Figure 9:
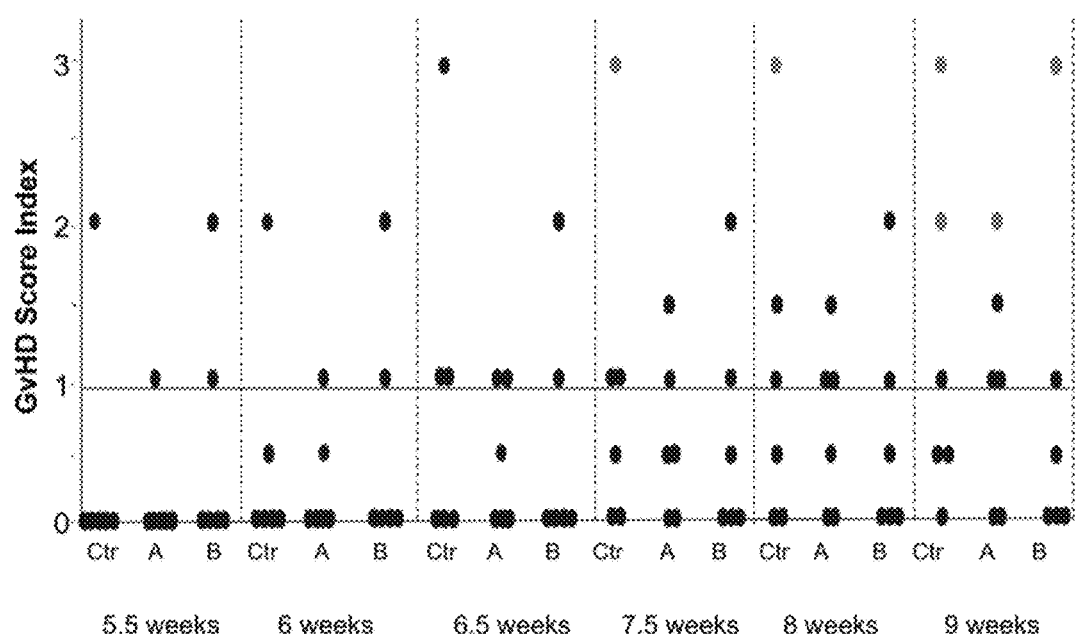
FIG. 9. Comparative effects of low-dose STRO-1 negative MSC (preparation A) and STRO-1$^{bright}$ MPC (preparation B) on GvHD. T-cell depleted bone marrow mononuclear cells (BMMC) ($5 \times 10^6$) and splenocytes ($30 \times 10^6$) from B10.D2 (H2d) donors were injected intravenously into lethally irradiated (750 cGy) BALB/c (H2d) recipient mice. After 4 weeks, recipient mice were injected with $0.3 \times 10^6$ cells of preparations A or B (A0.3,B0.3) or received no further treatment (Control 2). Six mice per group were injected. The graph reports the GvHD score per each mouse.
Figure 10:
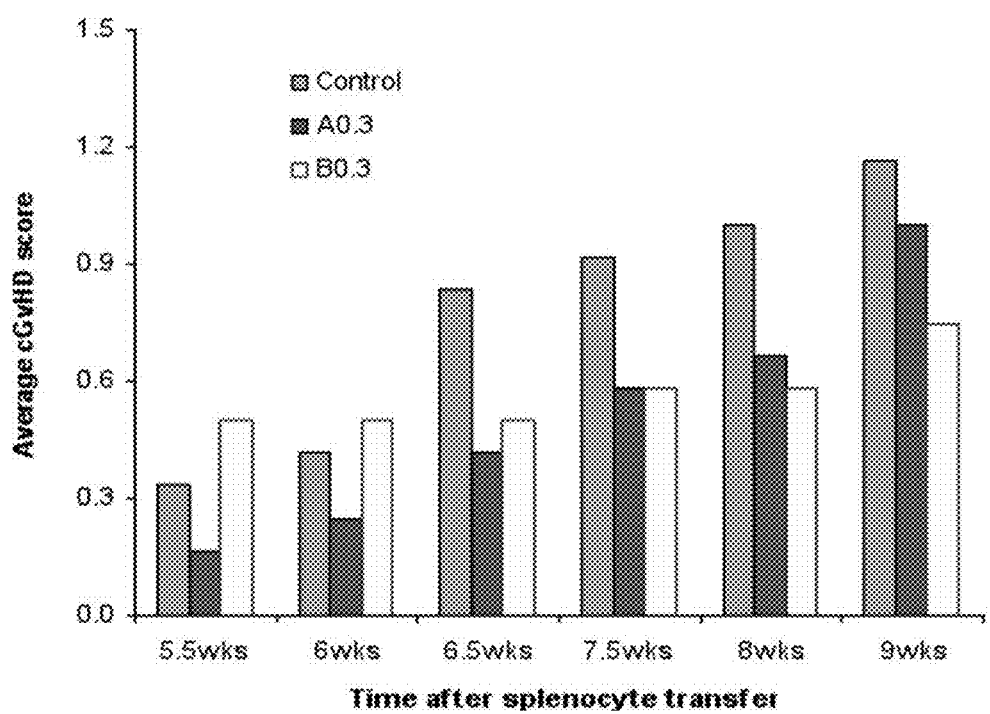
FIG. 10 Comparative effects of low-dose STRO-1 negative MSC (preparation A) and STRO-1$^{bright}$ MPC (preparation B) on GvHD. T-cell depleted bone marrow mononuclear cells (BMMC) ($5 \times 10^6$) and splenocytes ($30 \times 10^6$) from B10.D2 (H2d) donors were injected intravenously into lethally irradiated (750 cGy) BALB/c (H2d) recipient mice. After 4 weeks, recipient mice were injected with $0.3 \times 10^6$ cells of preparations A or B (A0.3, B0.3) or received no further treatment (Control 2). Six mice per group were injected. The graph reports the average GvHD score in each group.

Lastly, the injection of a lower dose (0.3×10$^6$ per mouse) again demonstrated that by 9 weeks STRO-1$^{bright}$ MPCs (B) had a superior effect on GVHD score reduction than A (FIGS. 9 and 10).

The data of this pilot study have consistently shown that STRO-1$^{bright}$ MPCs exhibited superior immunosuppressive capacities as compared to either no treatment or treatment with STRO-1 negative MSCs. This was evident in the in vitro assay and, most importantly in the in vivo assay. STRO-1$^{bright}$ MPCs produced a dramatic clinical effect on the prevention of GvHD given at dose ranges of 0.3-2×10$^6$ cells per mouse.

All references cited in this document are incorporated herein by reference.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for preventing the development of or treating graft versus host disease (GvHD) complications in a human patient undergoing or about to undergo a bone marrow or hematopoietic stem cell transplantation, which method comprises administering, to the human patient, a therapeutically effective amount of a population of cells enriched for STRO-1$^+$, TNAP$^+$ mesenchymal precursor cells (MPCs), or multipotential cells culture-expanded from STRO-1$^+$, TNAP$^+$ MPCs, wherein the cells in the administered population are CD34$^-$.

2. The method according to claim 1, wherein the administered population is administered to the human patient prior to undergoing the transplantation.

3. The method according to claim 1, wherein the bone marrow or hematopoietic stem cell transplantation is an allogeneic transplantation.

4. The method according to claim 1, wherein the administered population is allogeneic.

5. The methods according to claim 1, wherein the population is administered systemically.

6. The method according to claim 5, wherein the population is administered by intravenous injection.

7. The method of claim 1, wherein the administered population comprises between $0.1 \times 10^6$ to $5 \times 10^6$ cells.

8. The method of claim 1, wherein the administered population comprises between $0.3 \times 10^6$ to $2 \times 10^6$ cells.

9. The method of claim 1, wherein the administered population comprises between $0.1 \times 10^5$ and $0.5 \times 10^6$ cells.

10. The method of claim 9, wherein the administered population comprises about $0.3 \times 10^6$ cells.

11. The method of claim 1, wherein the administered population is administered once weekly or less often.

12. The method according to claim 1, wherein the human patient is suffering from aplastic anemia, myelofibrosis, or bone marrow failure following chemotherapy and radiation therapy.

13. The method according to claim 1, further comprising administering an immunosuppressive drug to the human patient.

* * * * *

```
                         SEQUENCE LISTING

<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 1
cactgacacg ttggcagtgg                                           20

<210> SEQ ID NO 2
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 2
catggagaag gctggggctc                                           20

<210> SEQ ID NO 3
<211> LENGTH: 20
<212> TYPE: DNA
<213> ORGANISM: Artificial Sequence
<220> FEATURE:
<223> OTHER INFORMATION: SDF-1 forward primer

<400> SEQUENCE: 3
gagacccgcg ctcgtccgcc                                           20

<210> SEQ ID NO 4
<211> LENGTH: 21
<212> TYPE: DNA
<213> ORGANISM: Artificial Sequence
<220> FEATURE:
<223> OTHER INFORMATION: SDF-1 reverse primer

<400> SEQUENCE: 4
gctggactcc tactgtaagg g                                         21

<210> SEQ ID NO 5
<211> LENGTH: 22
<212> TYPE: DNA
<213> ORGANISM: Artificial Sequence
<220> FEATURE:
<223> OTHER INFORMATION: IL-1B forward primer

<400> SEQUENCE: 5
aggaagatgc tggttccctc tc                                        22

<210> SEQ ID NO 6
<211> LENGTH: 23
<212> TYPE: DNA
<213> ORGANISM: Artificial Sequence
<220> FEATURE:
<223> OTHER INFORMATION: L-1B reverse primer

<400> SEQUENCE: 6
cagttcagtg atcgtacagg tgc                                       23
```

<210> SEQ ID NO 7
<211> LENGTH: 29
<212> TYPE: DNA
<213> ORGANISM: Artificial Sequence
<220> FEATURE:
<223> OTHER INFORMATION: FLT-1 forward primer

<400> SEQUENCE: 7
tcactatgga agatctgatt tcttacagt                              29

<210> SEQ ID NO 8
<211> LENGTH: 25
<212> TYPE: DNA
<213> ORGANISM: Artificial Sequence
<220> FEATURE:
<223> OTHER INFORMATION: FLT-1 reverse primer

<400> SEQUENCE: 8
ggtataaata cacatgtgct tctag                                  25

<210> SEQ ID NO 9
<211> LENGTH: 20
<212> TYPE: DNA
<213> ORGANISM: Artificial Sequence
<220> FEATURE:
<223> OTHER INFORMATION: TNF- forward primer

<400> SEQUENCE: 9
tcagatcatc ttctcgaacc                                        20

<210> SEQ ID NO 10
<211> LENGTH: 20
<212> TYPE: DNA
<213> ORGANISM: Artificial Sequence
<220> FEATURE:
<223> OTHER INFORMATION: TNF- reverse primer

<400> SEQUENCE: 10
cagatagatg ggctcatacc                                        20

<210> SEQ ID NO 11
<211> LENGTH: 20
<212> TYPE: DNA
<213> ORGANISM: Artificial Sequence
<220> FEATURE:
<223> OTHER INFORMATION: KDR forward primer

<400> SEQUENCE: 11
tatagatggt gtaacccgga                                        20

<210> SEQ ID NO 12
<211> LENGTH: 21
<212> TYPE: DNA
<213> ORGANISM: Artificial Sequence
<220> FEATURE:
<223> OTHER INFORMATION: KDR reverse primer

<400> SEQUENCE: 12
tttgtcactg agacagcttg g                                      21

<210> SEQ ID NO 13
<211> LENGTH: 21
<212> TYPE: DNA
<213> ORGANISM: Artificial Sequence
<220> FEATURE:
<223> OTHER INFORMATION: RANKL forward primer

```
<400> SEQUENCE: 13
aacaggcctt tcaaggagct g                                          21

<210> SEQ ID NO 14
<211> LENGTH: 22
<212> TYPE: PRT
<213> ORGANISM: Artificial Sequence
<220> FEATURE:
<223> OTHER INFORMATION: RANKL reverse primer

<400> SEQUENCE: 14

Thr Ala Ala Gly Gly Ala Gly Gly Gly Thr Thr Gly Gly Ala Gly
1               5                   10                  15

Ala Cys Cys Thr Cys Gly
            20

<210> SEQ ID NO 15
<211> LENGTH: 20
<212> TYPE: DNA
<213> ORGANISM: Artificial Sequence
<220> FEATURE:
<223> OTHER INFORMATION: leptin forward primer

<400> SEQUENCE: 15
atgcattggg aaccctgtgc                                            20

<210> SEQ ID NO 16
<211> LENGTH: 20
<212> TYPE: DNA
<213> ORGANISM: Artificial Sequence
<220> FEATURE:
<223> OTHER INFORMATION: leptin reverse primer

<400> SEQUENCE: 16
gcacccaggg ctgaggtcca                                            20

<210> SEQ ID NO 17
<211> LENGTH: 21
<212> TYPE: DNA
<213> ORGANISM: Artificial Sequence
<220> FEATURE:
<223> OTHER INFORMATION: CBFA-1 forward primer

<400> SEQUENCE: 17
gtggacgagg caagagtttc a                                          21

<210> SEQ ID NO 18
<211> LENGTH: 21
<212> TYPE: DNA
<213> ORGANISM: Artificial Sequence
<220> FEATURE:
<223> OTHER INFORMATION: CBFA-1 reverse primer

<400> SEQUENCE: 18
tggcaggtag gtgtggtagt g                                          21

<210> SEQ ID NO 19
<211> LENGTH: 28
<212> TYPE: DNA
<213> ORGANISM: Artificial Sequence
<220> FEATURE:
<223> OTHER INFORMATION: PPAR 2 forward primer

<400> SEQUENCE: 19
```
aactgcgggg aaacttggga gattctcc                                28

<210> SEQ ID NO 20
<211> LENGTH: 26
<212> TYPE: DNA
<213> ORGANISM: Artificial Sequence
<220> FEATURE:
<223> OTHER INFORMATION: PPAR 2 reverse primer

<400> SEQUENCE: 20
aataataagg tggagatgca ggctcc                                  26

<210> SEQ ID NO 21
<211> LENGTH: 21
<212> TYPE: DNA
<213> ORGANISM: Artificial Sequence
<220> FEATURE:
<223> OTHER INFORMATION: OCN forward primer

<400> SEQUENCE: 21
atgagagccc tcacactcct c                                       21

<210> SEQ ID NO 22
<211> LENGTH: 19
<212> TYPE: DNA
<213> ORGANISM: Artificial Sequence
<220> FEATURE:
<223> OTHER INFORMATION: OCN reverse primer

<400> SEQUENCE: 22
cgtagaagcg ccgataggc                                          19

<210> SEQ ID NO 23
<211> LENGTH: 20
<212> TYPE: DNA
<213> ORGANISM: Artificial Sequence
<220> FEATURE:
<223> OTHER INFORMATION: MyoD forward primer

<400> SEQUENCE: 23
aagcgccatc tcttgaggta                                         20

<210> SEQ ID NO 24
<211> LENGTH: 20
<212> TYPE: DNA
<213> ORGANISM: Artificial Sequence
<220> FEATURE:
<223> OTHER INFORMATION: MyoD reverse primer

<400> SEQUENCE: 24
gcgagaaacg tgaacctagc                                         20

<210> SEQ ID NO 25
<211> LENGTH: 20
<212> TYPE: DNA
<213> ORGANISM: Artificial Sequence
<220> FEATURE:
<223> OTHER INFORMATION: SMMHC forward primer

<400> SEQUENCE: 25
ctgggcaacg tagtaaaacc                                         20

<210> SEQ ID NO 26
<211> LENGTH: 20
<212> TYPE: DNA
<213> ORGANISM: Artificial Sequence
<220> FEATURE:
<223> OTHER INFORMATION: SMMHC reverse primer

<400> SEQUENCE: 26
tatagctcat tgcagcctcg                                           20

<210> SEQ ID NO 27
<211> LENGTH: 21
<212> TYPE: DNA
<213> ORGANISM: Artificial Sequence
<220> FEATURE:
<223> OTHER INFORMATION: GFAP forward primer

<400> SEQUENCE: 27
ctgttgccag agatggaggt t                                         21

<210> SEQ ID NO 28
<211> LENGTH: 20
<212> TYPE: DNA
<213> ORGANISM: Artificial Sequence
<220> FEATURE:
<223> OTHER INFORMATION: GFAP reverse primer

<400> SEQUENCE: 28
tcatcgctca ggaggtcctt                                           20

<210> SEQ ID NO 29
<211> LENGTH: 24
<212> TYPE: DNA
<213> ORGANISM: Artificial Sequence
<220> FEATURE:
<223> OTHER INFORMATION: nestin forward primer

<400> SEQUENCE: 29
ggcagcgttg gaacagaggt tgga                                      24

<210> SEQ ID NO 30
<211> LENGTH: 24
<212> TYPE: DNA
<213> ORGANISM: Artificial Sequence
<220> FEATURE:
<223> OTHER INFORMATION: nestin reverse primer

<400> SEQUENCE: 30
ctctaaactg gagtggtcag ggct                                      24

<210> SEQ ID NO 31
<211> LENGTH: 21
<212> TYPE: DNA
<213> ORGANISM: Artificial Sequence
<220> FEATURE:
<223> OTHER INFORMATION: SOX9 forward primer

<400> SEQUENCE: 31
ctctgcctgt ttggactttg t                                         21

<210> SEQ ID NO 32
<211> LENGTH: 21
<212> TYPE: DNA
<213> ORGANISM: Artificial Sequence
<220> FEATURE:
<223> OTHER INFORMATION: SOX9 reverse primer

<400> SEQUENCE: 32
cctttgcttg ccttttacct c                                         21

```
<210> SEQ ID NO 33
<211> LENGTH: 20
<212> TYPE: DNA
<213> ORGANISM: Artificial Sequence
<220> FEATURE:
<223> OTHER INFORMATION: collagen type X forward primer

<400> SEQUENCE: 33
agccagggtt gccaggacca                                                   20

<210> SEQ ID NO 34
<211> LENGTH: 20
<212> TYPE: DNA
<213> ORGANISM: Artificial Sequence
<220> FEATURE:
<223> OTHER INFORMATION: collagen type x reverse primer

<400> SEQUENCE: 34
ttttcccact ccaggagggc                                                   20

<210> SEQ ID NO 35
<211> LENGTH: 20
<212> TYPE: DNA
<213> ORGANISM: Artificial Sequence
<220> FEATURE:
<223> OTHER INFORMATION: aggrecan forward primer

<400> SEQUENCE: 35
cactgttacc gccacttccc                                                   20

<210> SEQ ID NO 36
<211> LENGTH: 20
<212> TYPE: DNA
<213> ORGANISM: Artificial Sequence
<220> FEATURE:
<223> OTHER INFORMATION: aggrecan reverse primer

<400> SEQUENCE: 36
accagcggaa gtccccttcg                                                   20
```